(12) United States Patent
Cho et al.

(10) Patent No.: US 11,782,013 B2
(45) Date of Patent: Oct. 10, 2023

(54) SENSOR DEVICE WITH BIOPOLYMER-METAL COMPOSITE FILM AND RELATED METHODS

(71) Applicant: UNIVERSITY OF CENTRAL FLORIDA RESEARCH FOUNDATION, INC., Orlando, FL (US)

(72) Inventors: Hyoung Jin Cho, Orlando, FL (US); Woo Hyoung Lee, Orlando, FL (US); Xiaochen Wang, Orlando, FL (US); Jae-Hoon Hwang, Orlando, FL (US); Pawan Pathak, Orlando, FL (US)

(73) Assignee: UNIVERSITY OF CENTRAL FLORIDA RESEARCH FOUNDATION, INC., Orlando, FL (US)

(*) Notice: Subject to any disclaimer, the term of this patent is extended or adjusted under 35 U.S.C. 154(b) by 226 days.

(21) Appl. No.: 16/532,578

(22) Filed: Aug. 6, 2019

(65) Prior Publication Data

US 2020/0049652 A1 Feb. 13, 2020

Related U.S. Application Data

(60) Provisional application No. 62/715,958, filed on Aug. 8, 2018.

(51) Int. Cl.
| | | |
|---|---|---|
| *G01N 27/333* | (2006.01) | |
| *G01N 27/30* | (2006.01) | |
| *G01N 27/406* | (2006.01) | |

(52) U.S. Cl.
CPC ....... *G01N 27/3335* (2013.01); *G01N 27/307* (2013.01); *G01N 27/4065* (2013.01)

(58) Field of Classification Search
CPC ............... G01N 27/307; G01N 27/333; G01N 27/3335; G01N 27/4065
See application file for complete search history.

(56) References Cited

U.S. PATENT DOCUMENTS

| | | | |
|---|---|---|---|
| 5,828,798 A | 10/1998 | Hopenfeld | |
| 7,666,285 B1* | 2/2010 | Cho | B01L 3/502715 137/833 |
| 9,603,243 B2 | 3/2017 | Kaplan et al. | |
| 9,891,215 B2* | 2/2018 | Kayyem | G01N 33/5438 |
| 2010/0207171 A1* | 8/2010 | Chou | G01N 27/3335 257/253 |
| 2011/0308942 A1 | 12/2011 | Liu et al. | |

(Continued)

OTHER PUBLICATIONS

C. Hao, A glassy carbon electrode modified with bismuth oxide nanoparticles and chitosan as a sensor for Pb(II) and Cd(II), Microchim Acta, 2016(183),m p. 1823-30. (Year: 2016).*

(Continued)

*Primary Examiner* — Caitlyn Mingyun Sun
(74) *Attorney, Agent, or Firm* — Allen, Dyer, Doppelt + Gilchrist, PA

(57) ABSTRACT

A sensor device is for detecting metal. The sensor device may have a substrate, an electrode on the substrate, and a biopolymer-metal composite film on the electrode. The biopolymer-metal composite film may include a metal and a biopolymer. The sensor device may further have circuitry coupled to the electrode and configured to apply a sensing signal to the electrode.

20 Claims, 29 Drawing Sheets

(56) References Cited

U.S. PATENT DOCUMENTS

| | | | | |
|---|---|---|---|---|
| 2016/0209346 | A1* | 7/2016 | Brondum | G01N 27/4166 |
| 2016/0317068 | A1* | 11/2016 | Pepin | H01L 23/29 |
| 2017/0102350 | A1* | 4/2017 | Lu | G01N 33/573 |
| 2017/0121754 | A1* | 5/2017 | Feldman | G01N 27/3275 |
| 2018/0105941 | A1* | 4/2018 | Chen | C25B 3/29 |

OTHER PUBLICATIONS

G-H Hwang, An electrochemical sensor based on the reduction of screen-printed bismuth oxide for the determination of trace lead and cadmium, Sensors and Actuators B, 2008(135), p. 309-16. (Year: 2008).*

S. Laschi, Gold-based screen-printed sensor for detection of trace lead, Sensors and Actuators B, 2006 (114), p. 460-65. (Year: 2006).*

C. Hao, A glassy carbon electrode modified with bismuth oxide nanoparticles and chitosan as a sensor for Pb(II) and Cd(II), Microchim Acta 2016 (183), p. 1823-1830. (Year: 2016).*

S. D. Richardson, "Disinfection by-products and other emerging contaminants in drinking water," TrAC Trends in Analytical Chemistry, vol. 22, No. 10, pp. 666-684, 2003.

Edwards, et al, "Elevated blood lead in young children due to lead-contaminated drinking water: Washington, DC, 2001-2004," Environmental science & technology, vol. 43, No. 5, pp. 1618-1623, 2009.

Anonymous—USEPA, "40 CFR Part 141 Subpart I—Control of Lead and Copper" National Primary Drinking Water Regulations, 2012. https://ecfr.io/Title-40/pt40.25.141; pp. 225.

Liu et al., "Innovative solid-state microelectrode for nitrite determination in a nitrifying granule," Environmental science & technology, vol. 42, No. 12, pp. 4467-4471, 2008.

Silva, et al. "Electrochemical determination of nitrites in natural waters with ultramicroelectrodes," Electroanalysis, vol. 8, No. 11, pp. 1055-1059, 1996.

Wang, et al. "Bismuth-coated carbon electrodes for anodic stripping voltammetry," Analytical chemistry, vol. 72, No. 14, pp. 3218-3222, 2000.

Hwang, et al. "An electrochemical sensor based on the reduction of screen-printed bismuth oxide for the determination of trace lead and cadmium," Sensors and Actuators B: Chemical, vol. 135, No. 1, pp. 309-316, 2008.

Varma, et al. "Metal complexation by chitosan and its derivatives: a review," Carbohydrate Polymers, vol. 55, No. 1, pp. 77-93, 2004.

Vicentini, et al. "Pb (II) determination in natural water using a carbon nanotubes paste electrode modified with crosslinked chitosan," Microchemical Journal, vol. 116, pp. 191-196, 2014.

Ghalkhani et al. "Adsorptive stripping differential pulse voltammetric determination of mebendazole at a graphene nanosheets and carbon nanospheres/chitosan modified glassy carbon electrode," Sensors and Actuators B: Chemical, vol. 185, pp. 669-674, 2013.

Kadara, et al. "Characterization and fabrication of disposable screen printed microelectrodes," Electrochemistry Communications, vol. 11, No. 7, pp. 1377-1380, 2009.

Janegitz, et al. "Anodic stripping voltammetric determination of copper (II) using a functionalized carbon nanotubes paste electrode modified with crosslinked chitosan," Sensors and Actuators B: Chemical, vol. 142, No. 1, pp. 260-266, 2009.

Zanini, et al. "Enhancement of amperometric response to tryptophan by proton relay effect of chitosan adsorbed on glassy carbon electrode," Sensors and Actuators B: Chemical, vol. 209, pp. 391-398, 2015.

Luo, et al. "An effective and recyclable adsorbent for the removal of heavy metal ions from aqueous system: magnetic chitosan/cellulose microspheres ," Bioresource technology, vol. 194, pp. 403-406, 2015.

Tran et al. "Typical low cost biosorbents for adsorptive removal of specific organic pollutants from water," Bioresource technology, vol. 182, pp. 353-363, 2015.

Wu, et al. "Electrochemical detection of heavy metal pollutant using crosslinked chitosan/carbon nanotubes thin film electrodes," Materials Express, vol. 7, No. 1, pp. 15-24, 2017.

Khaled, et al. "Chitosan modified screen-printed carbon electrode for sensitive analysis of heavy metals," Int. J. Electrochem. Sci, vol. 5, No. 2, pp. 158-167, 2010.

Hwang, et al, "Enhanced electrochemical detection of multi-heavy metal ions using a biopolymer-coated planar carbon electrode," In Sensors Applications Symposium (SAS), 2018 IEEE, 2018, pp. 1-6: IEEE.

Yasmeen, et al. "Chromium (VI) ions removal from tannery effluent using chitosan-microcrystalline cellulose composite as adsorbent," Int. Res. J. Pure Appl. Chem, vol. 10, No. 4, pp. 1-14, 2016.

Wei, et al. "Selective detection toward Hg (II) and Pb (II) using polypyrrole/carbonaceous nanospheres modified screen-printed electrode," Electrochimica Acta, vol. 105, pp. 218-223, 2013.

Koper, et al. "Effects of ambient noise on detectability and localization of avian songs and tones by observers in grasslands," Ecology and evolution, vol. 6, No. 1, pp. 245-255, 2016.

Lee, et al. "Amperometric carbon fiber nitrite microsensor for in situ biofilm monitoring," Sensors and Actuators B: Chemical, vol. 188, pp. 1263-1269, 2013.

Martínez-Huitle, et al. "Determination of trace metals by differential pulse voltammetry at chitosan modified electrodes," Portugaliae Electrochimica Acta, vol. 28, No. 1, pp. 39-49, 2010.

Vilar, et al. "Continuous biosorption of single and binary metal solutions in a fixed-bed column using algae gelidium and granulated algal waste from agar extraction," Water Resources Research Progress, pp. 275-296, 2008.

Munoz et al. "Determination of heavy metals in honey by potentiometric stripping analysis and using a continuous flow methodology" Food Chemistry 94 (2006) 478-483.

\* cited by examiner

SENSOR DEVICE WITH BIOPOLYMER-METAL COMPOSITE FILM AND RELATED METHODS

RELATED APPLICATION

This application is based upon prior filed copending Application No. 62/715,958 filed Aug. 8, 2018, the entire subject matter of which is incorporated herein by reference in its entirety.

TECHNICAL FIELD

The present disclosure relates to the field of sensors, and, more particularly, to chemical sensors and related methods.

BACKGROUND

Among available analytical methods for water quality monitoring, those based on electrochemistry are considered complementary to the traditional techniques (e.g., inductively coupled plasma (ICP) and atomic absorption spectroscopy (AAS)), promising less expensive and portable instruments. Particularly, square-wave anodic stripping voltammetry (SWASV) sensors with metallic mercury have been developed for heavy metal detection. However, due to the toxicity of mercury, environmentally benign materials that can replace mercury for heavy metal sensing materials may be helpful.

One alternative to mercury electrode materials for microsensors for water quality monitoring is bismuth. This is due to bismuth's ability to form alloys with a variety of heavy metals, wide potential window applicable to electrochemical detection, and low toxicity. Bismuth is a pentavalent post-transition metal, and is one of the pnictogens with chemical properties resembling its lighter homologs being arsenic and antimony.

SUMMARY

Generally, a sensor device for detecting metal may include a substrate, at least one electrode on the substrate, and a biopolymer-metal composite film on the at least one electrode. The biopolymer-metal composite film may comprise a metal and a biopolymer. The sensor device may further comprise circuitry coupled to the at least one electrode and configured to apply a sensing signal to the at least one electrode.

In some embodiments, the biopolymer comprises at least one of a polysaccharide material, a chitosan material, and a chitin material. The metal may comprise at least one of iron, copper, and bismuth.

Additionally, the at least one electrode may include a multi-layer electrode. The multi-layer electrode may include an electrically conductive layer on the substrate, an electrode layer on the electrically conductive layer, and an insulator layer over the electrically conductive layer. The electrode layer may comprise carbon. The electrode layer may include gold. The circuitry may be configured to generate the sensing signal to comprise a SWASV sensing signal. For example, the substrate may comprise a dielectric material, such as a polymer plastic material. In some embodiments, the counter electrode may comprise a distal end being spaced apart from the reference electrode. The counter electrode may be C-shaped.

One aspect is directed to a water sensor device for detecting heavy metal in a water sample. The water sensor device comprises a substrate, a reference electrode on the substrate, a counter electrode on the substrate, and at least one multi-layer electrode on the substrate and being between the reference electrode and the counter electrode. The counter electrode curves around the at least one multi-layer electrode. The at least one multi-layer electrode comprises an electrically conductive layer on the substrate, an electrode layer on the electrically conductive layer, the electrode layer being directly on the electrically conductive layer and contacting the substrate on opposite sides of the electrically conductive layer, and an insulator layer contacting the electrode layer and the substrate, and defining an opening over the electrode layer. The water sensor also includes a biopolymer-metal composite film on the at least one multi-layer electrode and directly on the insulator layer. The biopolymer-metal composite film extends through the opening and contacts the electrode layer and the insulator layer. The biopolymer-metal composite film comprises a metal and a biopolymer, the metal comprising iron, the biopolymer comprising a chitosan material. A width of the opening is less than a width of the biopolymer-metal composite film. The water sensor further comprises circuitry coupled to the at least one multi-layer electrode and configured to apply a sensing signal to the at least one multi-layer electrode to detect the metal in the water sample, the heavy metal comprising at least lead.

Another aspect is directed to a method for making a sensor device for detecting metal. The method may include forming at least one electrode on a substrate, and forming a biopolymer-metal composite film on the at least one electrode. The biopolymer-metal composite film may include a metal and a biopolymer. The method may comprise coupling circuitry to the at least one electrode. The circuitry may be configured to apply a sensing signal to the at least one electrode.

The forming of the biopolymer-metal composite film on the at least one electrode may include an electrodeposition process. The electrodeposition process may include positioning the at least one electrode and the substrate in a solution. The solution may comprise ions of the metal, and the biopolymer. The electrodeposition process may include applying an electrical current between the at least one electrode defining a cathode and an anode electrode. The forming of the at least one electrode may include a screen printing process.

BRIEF DESCRIPTION OF THE DRAWINGS

FIGS. 1A-1C are images of layer patterns for a sensor device.

DETAILED DESCRIPTION

The present disclosure will now be described more fully hereinafter with reference to the accompanying drawings, in which several embodiments of the invention are shown. This present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art. Like numbers refer to like elements throughout.

Generally, the brittleness and detachment of conventional microsensors that use bismuth as an electrode is recognized to impose practical problems for industrial applications including for water quality monitoring. The microsensors disclosed herein may provide an approach to this issue. A thin film sensing device may include a substrate, at least one electrode (e.g., planar screen-printed carbon electrode) on the substrate, and a biopolymer-metal composite thin film on the electrode comprising at least one metal intermixed with a polysaccharide, which may be formed by co-electroplating metal and biopolymer on the substrate.

As a biopolymer is water soluble in adjusted pH conditions, it has a high mechanical strength and shows good adhesion to traditional electrochemical surfaces. The co-electroplating of the biopolymer-metal composite thin film prevents detachment problems of metal. In addition, the thin film of the biopolymer-metal composite improves ability to adsorb metal ions and thus increases the sensor detection sensitivity.

The biopolymer-metal composite may comprise integrated chitosan and bismuth, integrated chitosan and iron, integrated chitosan and other metals, which can be used for the simultaneous detection of a variety of heavy metal ions (e.g., Cd, Pb, Zn and As), such as using SWASV. Multiple heavy metal ions can be simultaneously detected including their concentrations with the presence of other ions in mining water, municipal wastewater, soil leachate and drinking water samples.

Figure 1D:
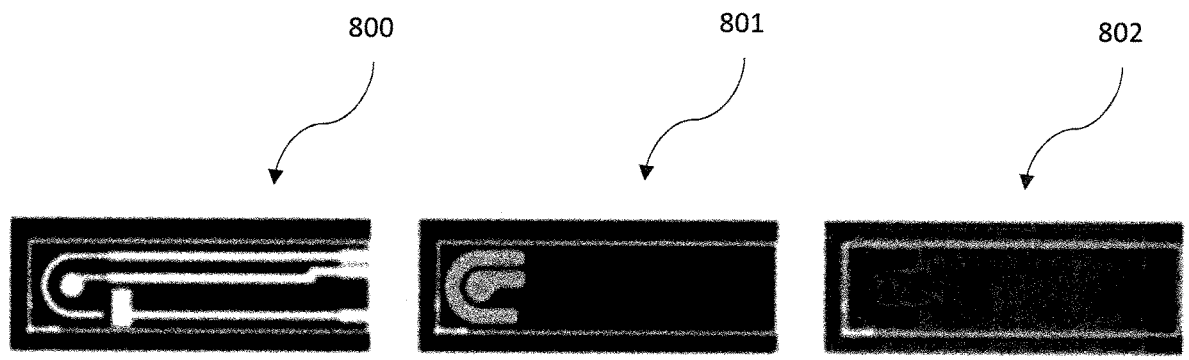
FIG. 1D is an image of a sensor device, according to an example embodiment of the present disclosure.
Figure 1D:
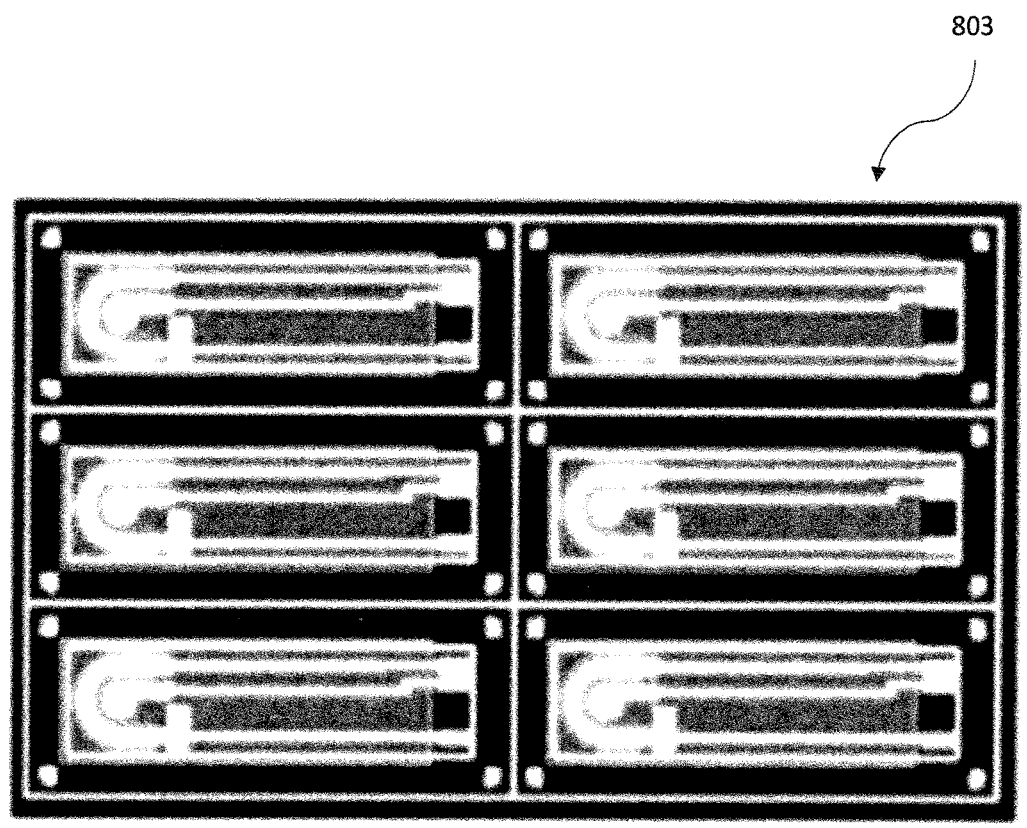

To form the biopolymer-metal composite on an electrode, a screen-printed carbon electrode can be used, as shown in the carbon patterns 800-803 of FIG. 1. The screen-printed carbon electrode is prepared by screen printing of silver, carbon, and an insulation layer serially on a polymer substrate. Generally, any patterns or configuration of a carbon electrode can be used to form a disclosed biopolymer-metal composition on it. In the screen-printed carbon electrode platform, a carbon electrode exposed with a 2 μm to 10 mm diameter can be used as the working electrode.

A nanostructured biopolymer/metal composite film can be formed by co-electrodeposition on this working electrode, and then patterned to form the biopolymer-metal pattern shown used for in situ determination of multiple heavy metals. The present disclosure also provides a simple electrodeposition method for an integrated biopolymer/metal composite film, which can be used aquatically to monitor the concentration of heavy metal ions, or for in situ analysis of leachate heavy metal ions in water. Although the biopolymer-metal composite is generally described as being deposited by an electrochemical deposition, other deposition methods are also possible, such as sputtering.

The electrolytes used during the electro co-deposition process have a metal ions source and polysaccharide. Polysaccharides, as will be appreciated by those skilled in the art, are polymeric carbohydrate molecules composed of long chains of monosaccharide units bound together by glycosidic linkages, which on hydrolysis give the constituent monosaccharides or oligosaccharides.

Metals that can be sensed comprise iron, copper, or bismuth, but are not limited to these metals. Polysaccharides include but is not limited to chitosan, and chitin. The metal source in an electrolyte is a salt ($M_xBy$) of a respective metal where, X, Y are numbers, and M is a metal ion of the metals described above, and B is an anion such as $NO_3$, Cl, or $HCO_3$. In some cases, salts may not be directly soluble in the low acetic acid solution but can be made soluble by using organic solvent. The organic solvent can compromise glycol, glycerol or any derivatives of these, or other organic solvents.

Different species of metal components in the composite film were used for the detection of different specific heavy metal ions. As an example, an iron based-composite for detecting arsenic and Bismuth-based composite for detecting zinc, cadmium and lead exhibited excellent representativeness and reproducibility for in situ multi heavy metal ions detection in concentrations as low as fraction of ppb.

As noted above, SWASV can be used for the simultaneous detection of a variety of heavy metal ions. SWASV involves adsorption of the analyte on the electrode surface, which is quantified by scanning or applying a square wave scan in the negative or positive direction to give a peak-shaped voltammetric response with an amplitude proportional to the concentration. The excitation signal in square-wave voltammetry comprises a symmetrical square-wave pulse of amplitude $E_{sw}$ superimposed on a staircase waveform of step height AE, where the forward pulse of the square wave coincides with the staircase step. The differential current (difference between the forward and reverse currents centered on the redox potential) is then plotted as a function of potential, and the reduction or oxidation of species is measured as a peak or trough. The peak height is directly proportional to the concentration of the electroactive species. Direct detection limits down to the ppb is possible. Square-wave voltammetry provides several advantages because of its excellent speed, enhanced sensitivity and the rejection of background currents.

Figure 2:
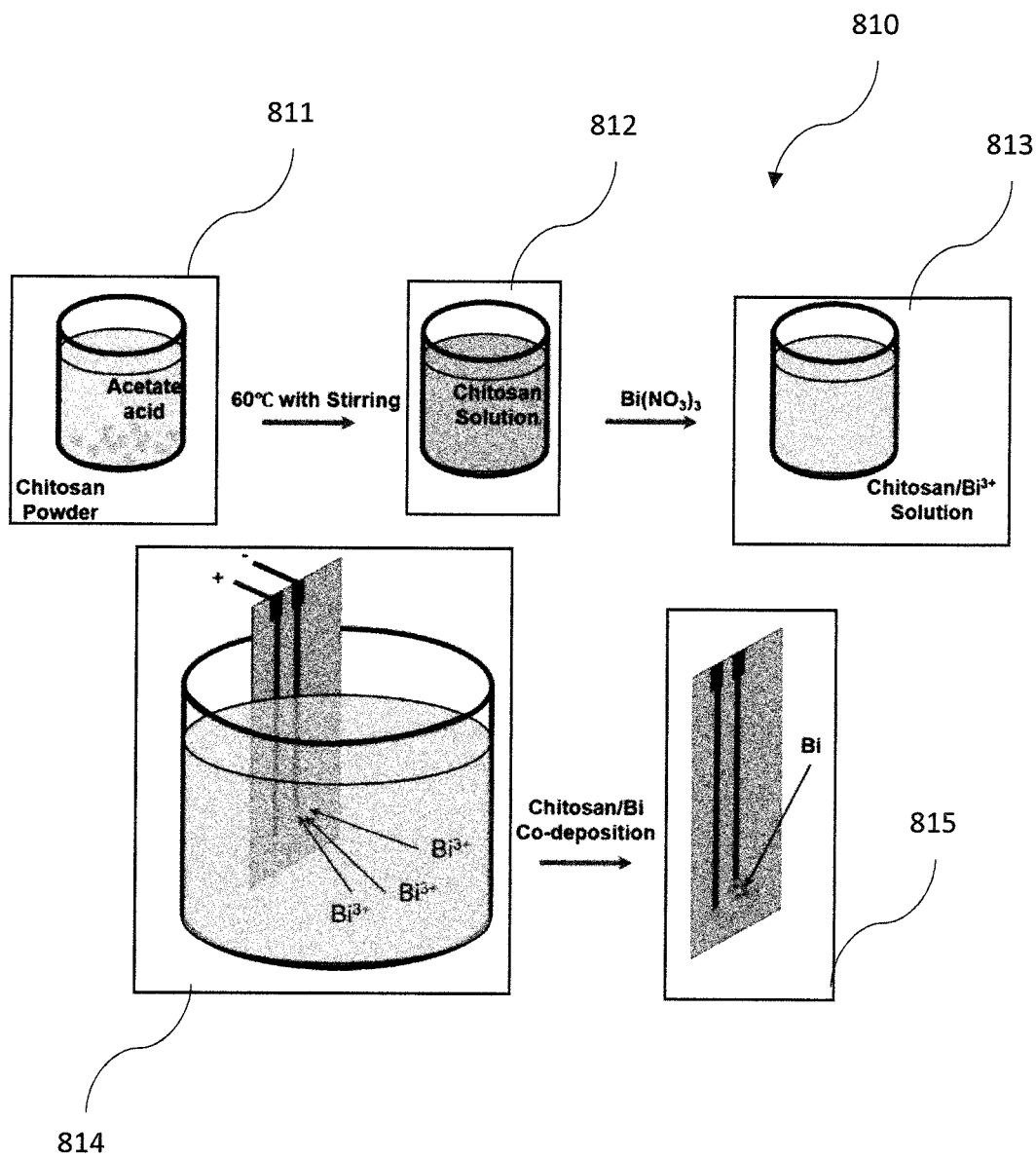
FIG. 2 is a schematic diagram of a method for making an example embodiment of the sensor device, according to the present disclosure.

An example electrode fabrication process for forming a bismuth/chitosan coated microsensor is shown in the diagram 810 of FIG. 2. An electrolyte can be prepared by dissolving 0.1M bismuth nitrate and 24 mg of chitosan in 20 mL of 0.1 M acetic acidy. Then, with a screen-printed carbon electrode as the cathode and embedded carbon electrode as anode, a current (100 $mAcm^{-2}$) was applied between electrodes for 30 s to deposit a bismuth/chitosan film on the carbon electrode surface using a potentiostat, such as the PalmSens EIS (as available from PalmSens Compact Electrochemical Interfaces from BASi Corporation of West Lafayette, Ind.). Other additives, such as glycerol, can be added into the electrolyte to enhance the quality of the co-electrodeposited biopolymer/metal composite film. To form an iron/chitosan coated biosensor, 0.1 M ferric chloride can be substituted for the 0.1M bismuth nitrate described above.

After plating bismuth/chitosan on the electrode, the surface of the carbon electrode is washed with deionized (DI) water to remove any residues on the electrode and then dried. The mechanism of chitosan/bismuth co-electrodeposition process is shown below in Equation (1)-(4), where chitosan is shown as 'Chi'.

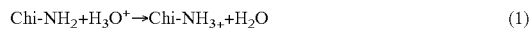
$$Chi\text{-}NH_2 + H_3O^+ \rightarrow Chi\text{-}NH_3^+ + H_2O \qquad (1)$$

$$2H_2O + 2e^- \rightarrow H_2 + 2OH^- \qquad (2)$$

$$Chi\text{-}NH_3^+ + OH^- \rightarrow Chi\text{-}NH_2 + H_2O \qquad (3)$$

$$Bi^{3+} + 3e^- \rightarrow Bi \qquad (4)$$

Chitosan generally has better dissolvability under acidic condition (Equation (1)) but forms a gel under alkaline condition (Equation (3)). Therefore, the electrochemistry process in Equation (2) was used that consumes the hydrogen ions at the electrode surface and forms a local high pH region that dissolved chitosan from the gel at the local region. At the same time, reaction in Equation (4) is also carried out. By combining the reactions in Equations (3) and (4) at the same time, the chitosan/bismuth composite film is co-electrodeposited on the electrode surface.

Figure 3A:
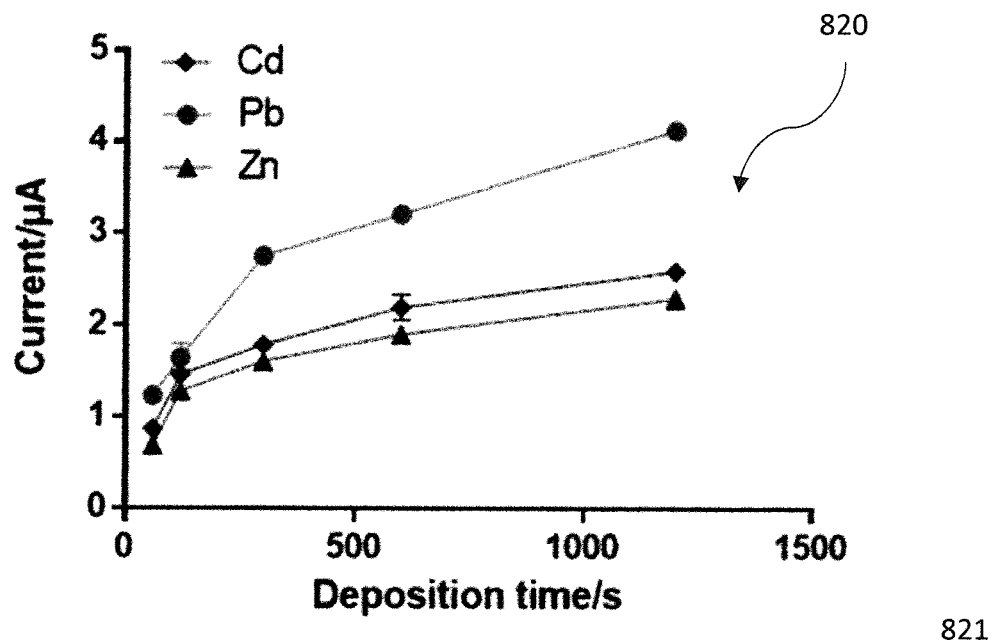
FIGS. 3A-3C are diagrams of effects of deposition time, amplitude, and frequency, respectively, on the stripping peak currents of $Zn^{2+}$, $Cd^{2+}$ and $Pb^{2+}$ of a bismuth/chitosan-coated carbon electrode in an example embodiment of the sensor device, according to the present disclosure.
Figure 3B:
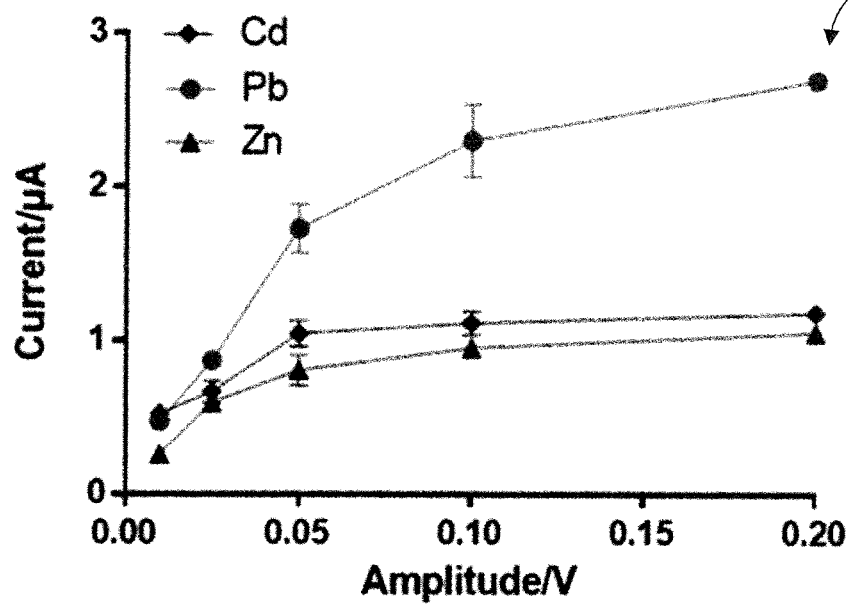
Figure 3C:
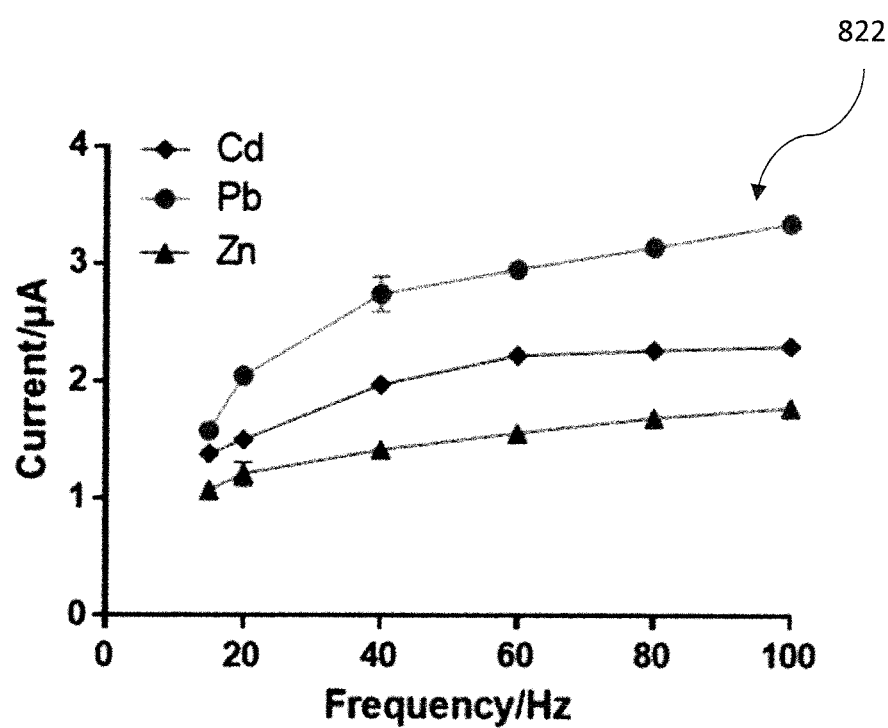
Figure 4A:
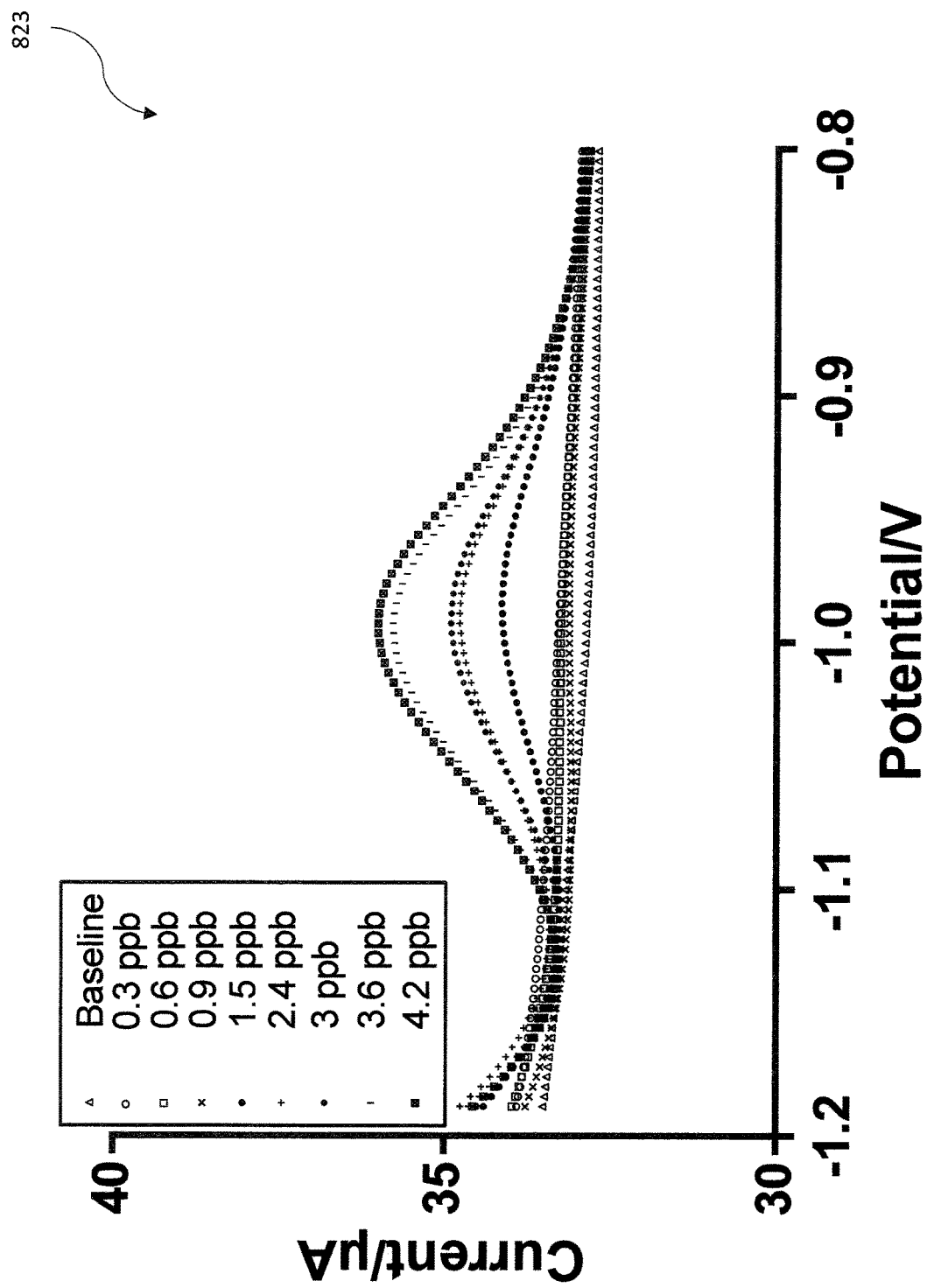
FIGS. 4A-4C are diagrams of differential pulse SWASV for $Pb^{2+}$, $Cd^{2+}$ and $Pb^{2+}$, respectively, in 0.1 M acetate buffer during a method for making the sensor device, according to the present disclosure.
Figure 4B:
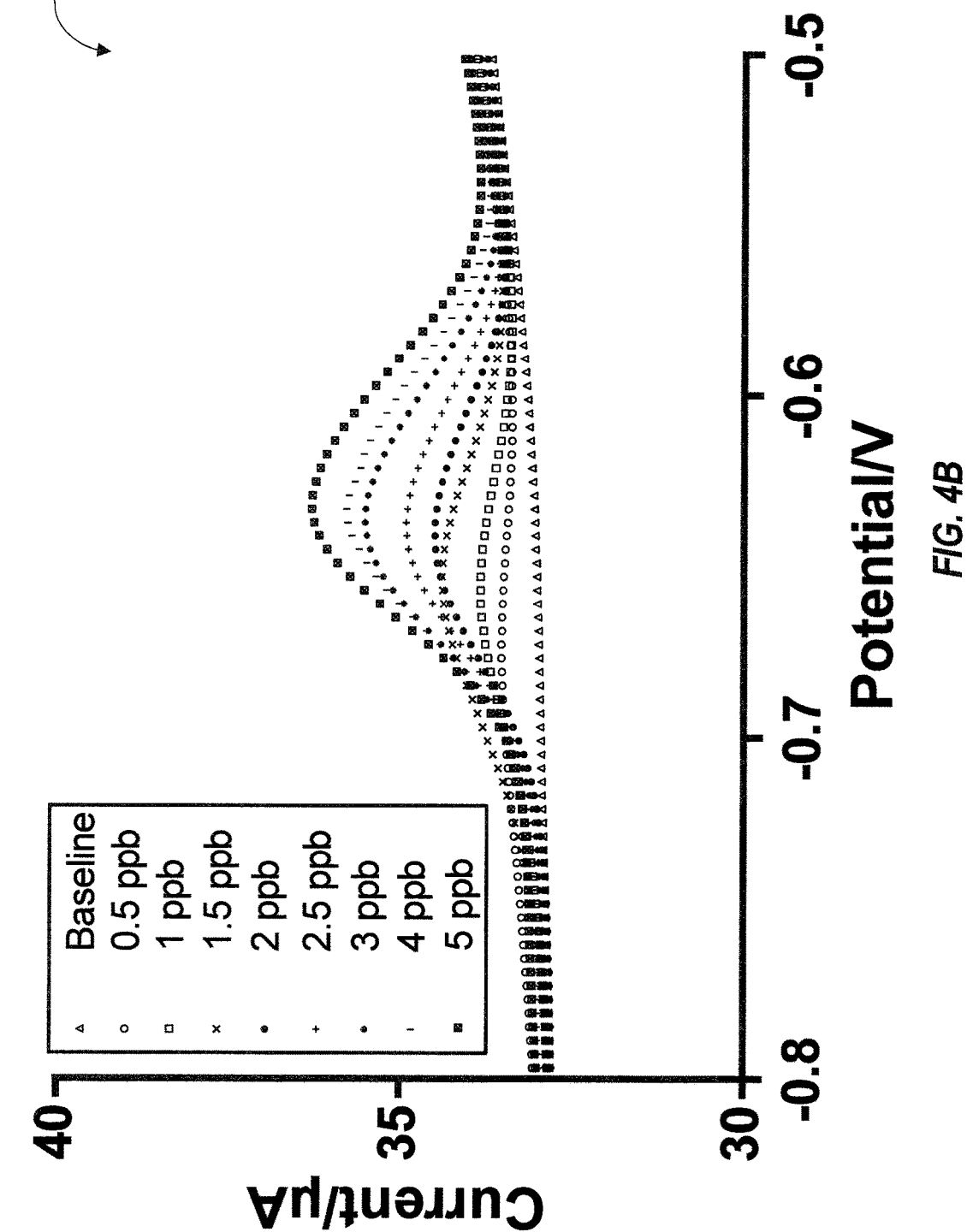
Figure 4C:
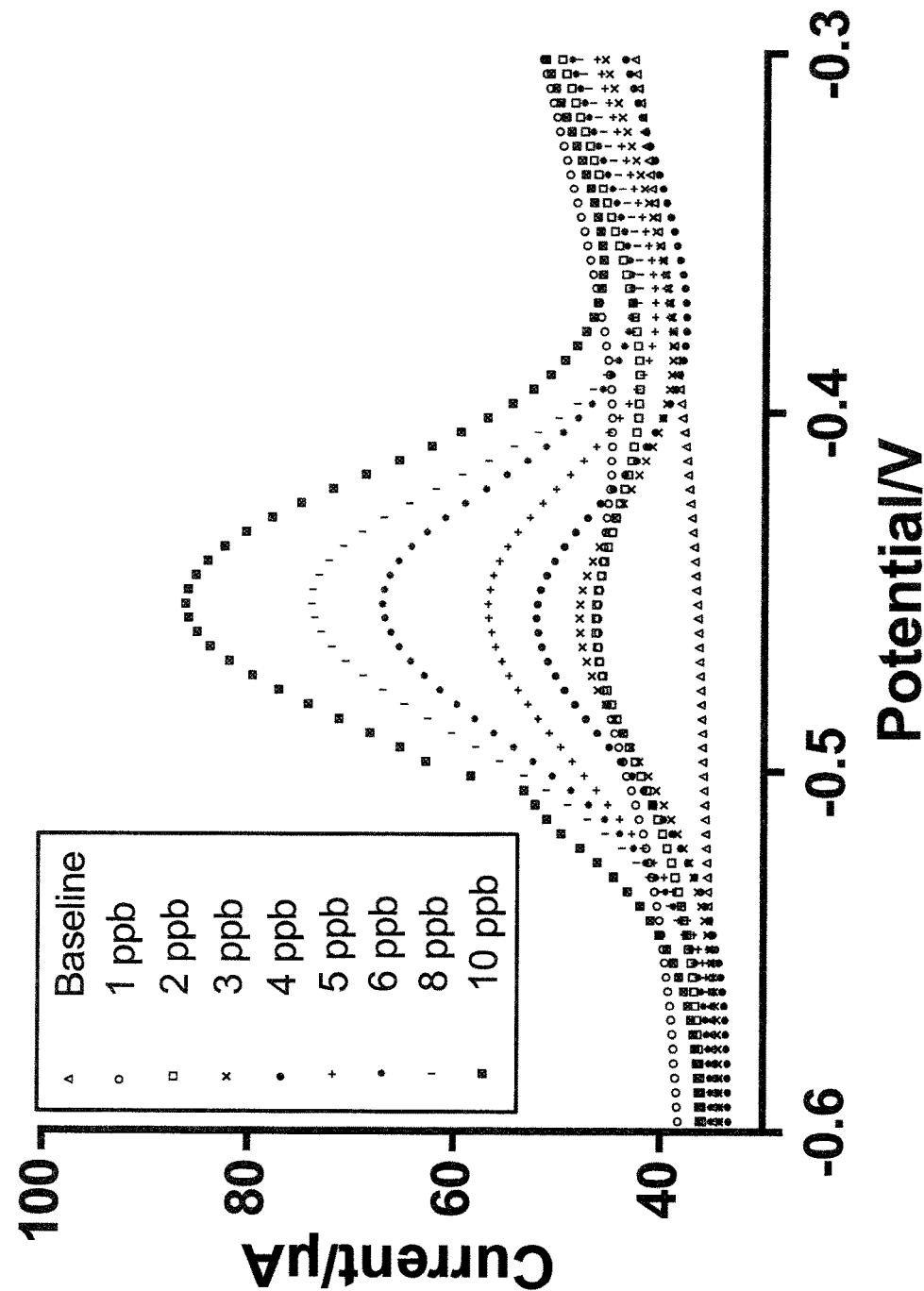
Figure 4D:
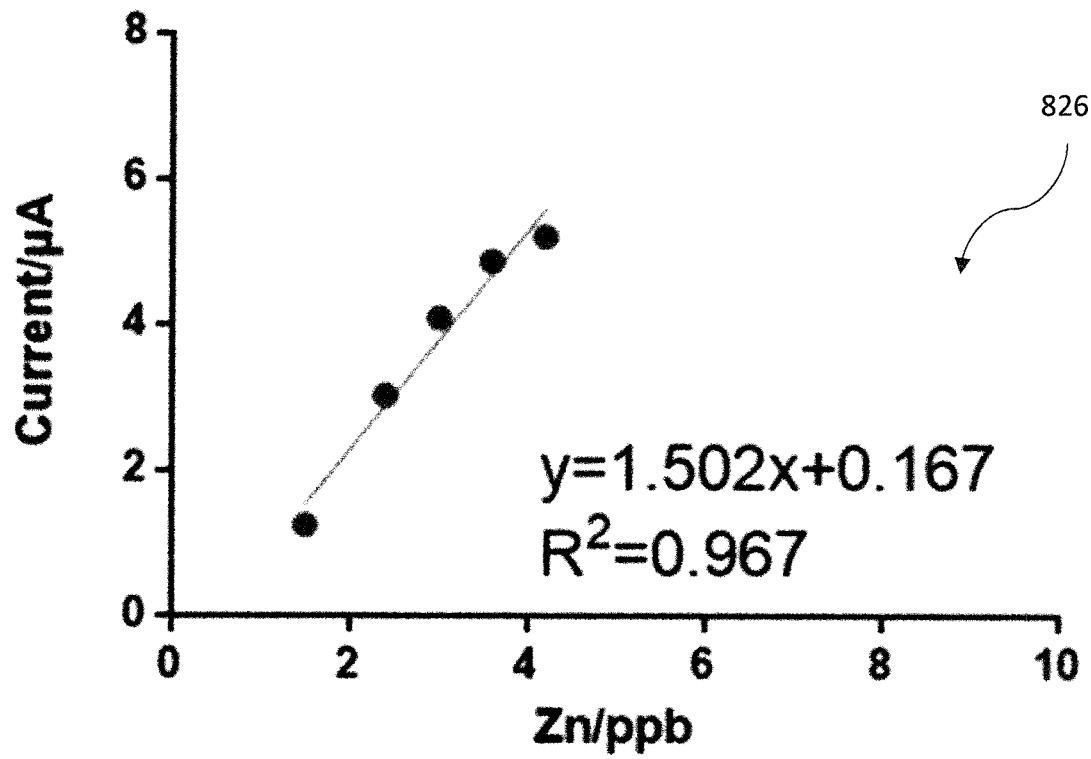
FIGS. 4D-4F are diagrams of calibration curves of $Pb^{2+}$, $Cd^{2+}$ and $Pb^{2+}$, respectively, in 0.1 M acetate buffer during a method for making the sensor device, according to the present disclosure.
Figure 4E:
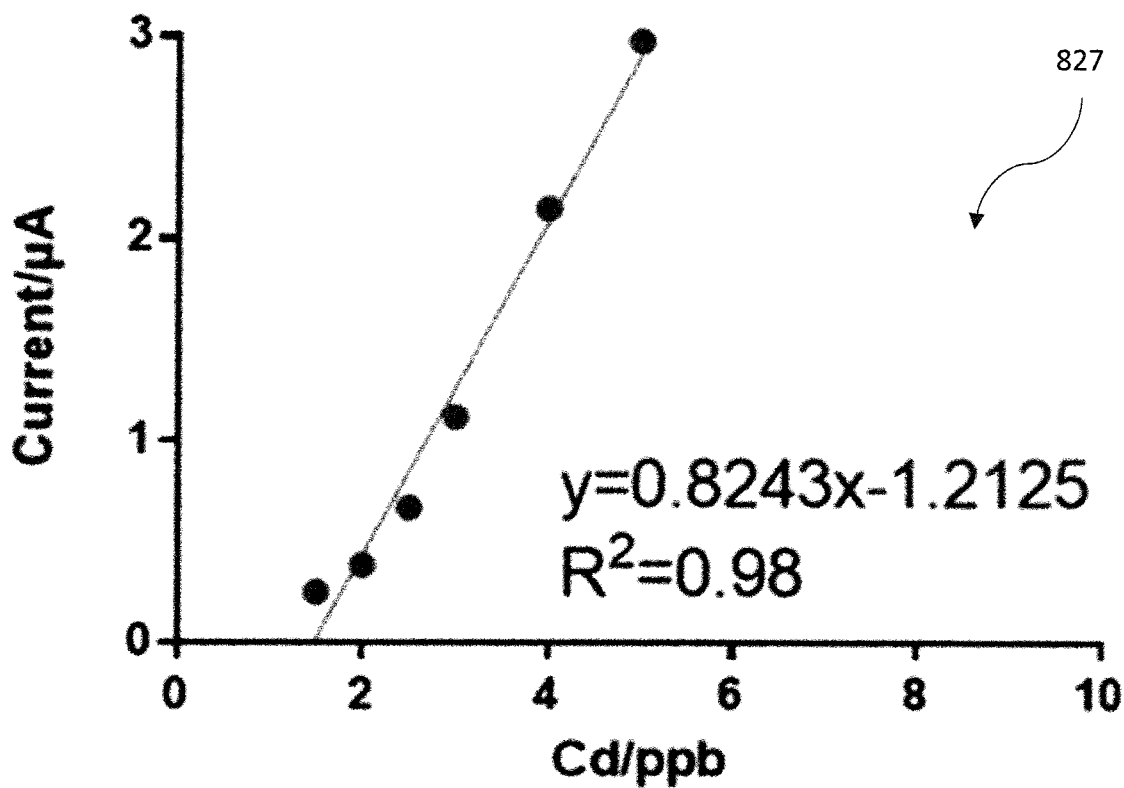
Figure 4F:
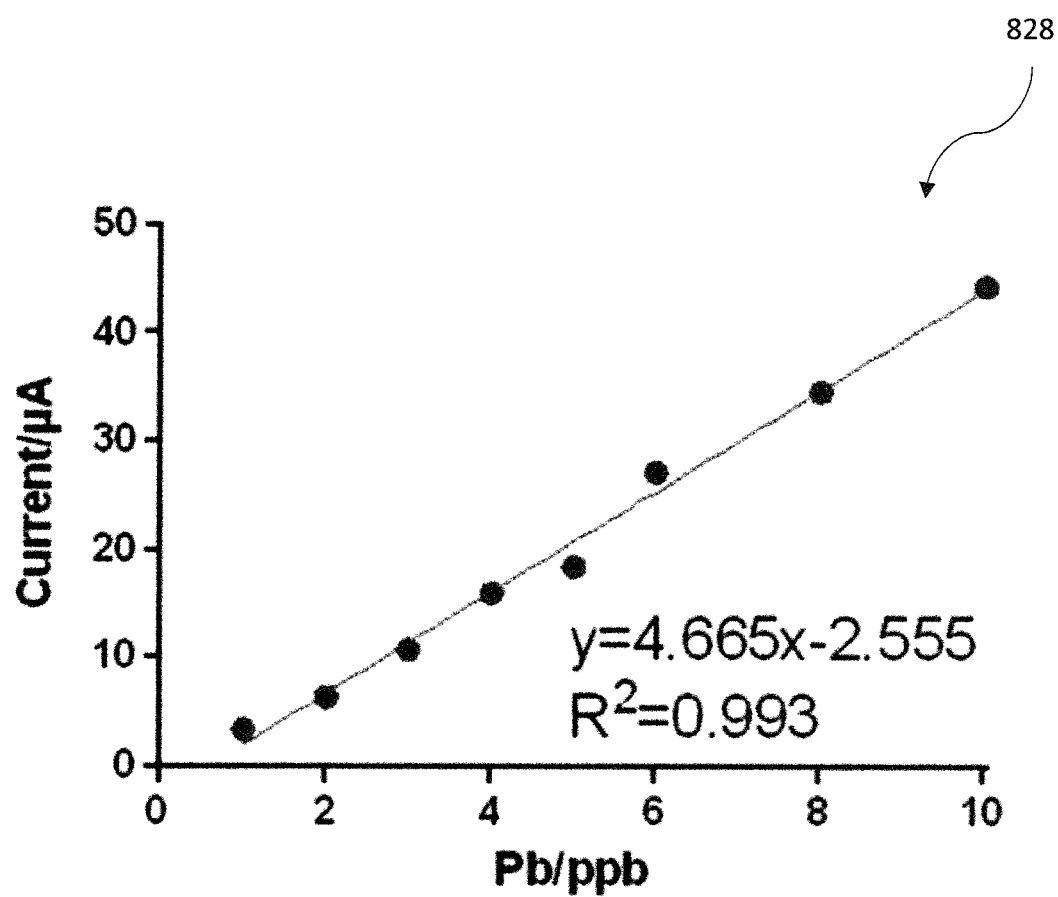

The bismuth, iron or other metal-chitosan coated carbon electrode electrodeposition working parameters include varying the deposition time, amplitude, and frequency for initial deposition which were evaluated. FIGS. 3A-3C and diagrams 820-822 show the influence of working on the stripping peak of $Zn^{2+}$, $Cd^{2+}$ and $Pb^{2+}$ ions. Experimentally defined −1.4 and +0.0 V were used as deposition and cleaning potentials, respectively. The peak currents of $Zn^{2+}$, $Cd^{2+}$ and $Pb^{2+}$ increased linearly from 1.2, 0.8 and 0.7 to 4.2, 2.6 and 2.2 µA with prolonged deposition time, respectively. The peak current for $Zn^{2+}$ and $Cd^{2+}$ initially increased with deposition time, then slightly increased after 120 s, probably due to the saturation of $Zn^{2+}$ and $Cd^{2+}$ on the electrode surface in FIG. 3A. In the case of $Pb^{2+}$, after 300 s of deposition time, the increase of peak currents was not significant compared to the currents measured after less than 300 s of deposition time. Thus, 300 s was selected for a deposition time for $Zn^{2+}$, $Cd^{2+}$ and $Pb^{2+}$ measurements.

The amplitude and frequency showed significant effects on the stripping response as shown in FIGS. 3B and 3C. The highest current was observed using 0.1 V amplitude and a 40 Hz frequency. Finally, 0.05 V of pulse amplitude and 20 Hz of frequency were selected for further evaluation of the biopolymer-coated sensor performance for in situ heavy metal detection.

The analytical performance of the bismuth-chitosan-coated carbon electrode was investigated by simultaneous analysis of $Zn^{2+}$, $Cd^{2+}$ and $Pb^{2+}$ concentrations from 1 ppb to 10 ppb in a 0.1 M acetate buffer solution. The deposition time was 300 s with a −1.4 V deposition potential, 0.004 V potential step, 0.5 V amplitude, and 20 Hz frequency. The well-defined sharp peaks for $Zn^{2+}$, $Cd^{2+}$ and $Pb^{2+}$ are located at ca. −1.0, −0.63 and −0.45V, respectively, shown in diagrams 823-828 of FIGS. 4A-4F, and the peak currents were proportionally increased with positive shifts of peak potentials as the concentration of heavy metal ions increase. The SWASV peak currents were obtained with correction to the baseline and then the calibration plots were evaluated from the peak currents. The corresponding calibration plots and correlation coefficients showed $R^2$=0.97, 0.98 and 0.99 for $Zn^{2+}$, $Cd^{2+}$ and $Pb^{2+}$. The limit of detection (LOD) was determined to be 1.5 ppb for $Zn^{2+}$ and 1.5 ppb for $Cd^{2+}$ and 1 ppb for $Pb^{2+}$ for simultaneous analysis.

Figure 5A:
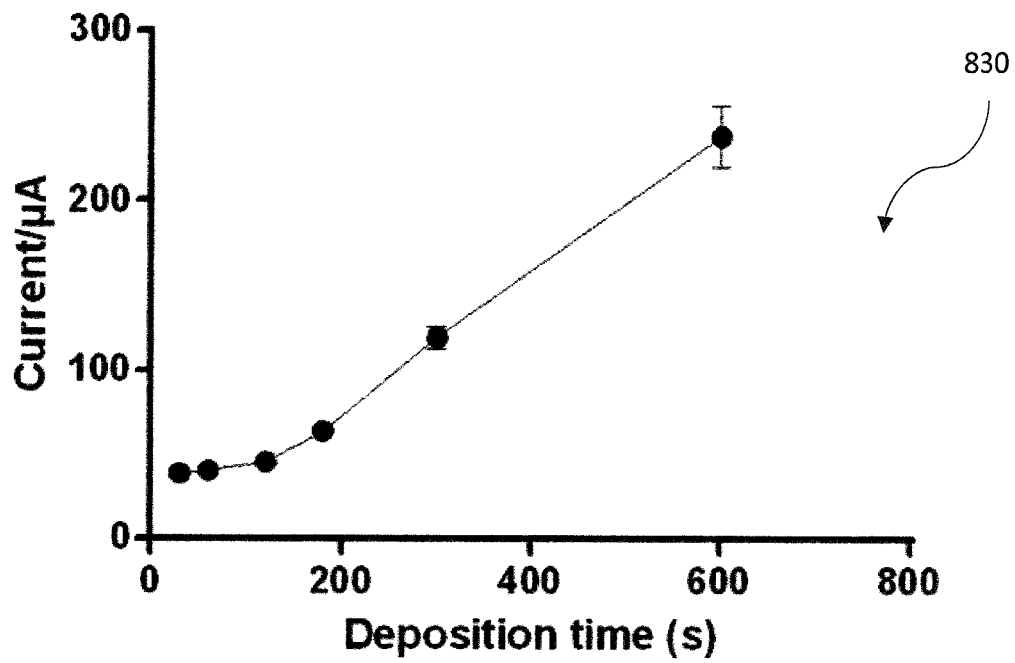
FIGS. 5A-5D are diagrams of effects of deposition time, amplitude, frequency and deposition time, respectively, on the stripping peak currents of $As^{3+}$ of the iron/chitosan-coated carbon electrode in an example embodiment of the sensor device, according to the present disclosure.
Figure 5B:
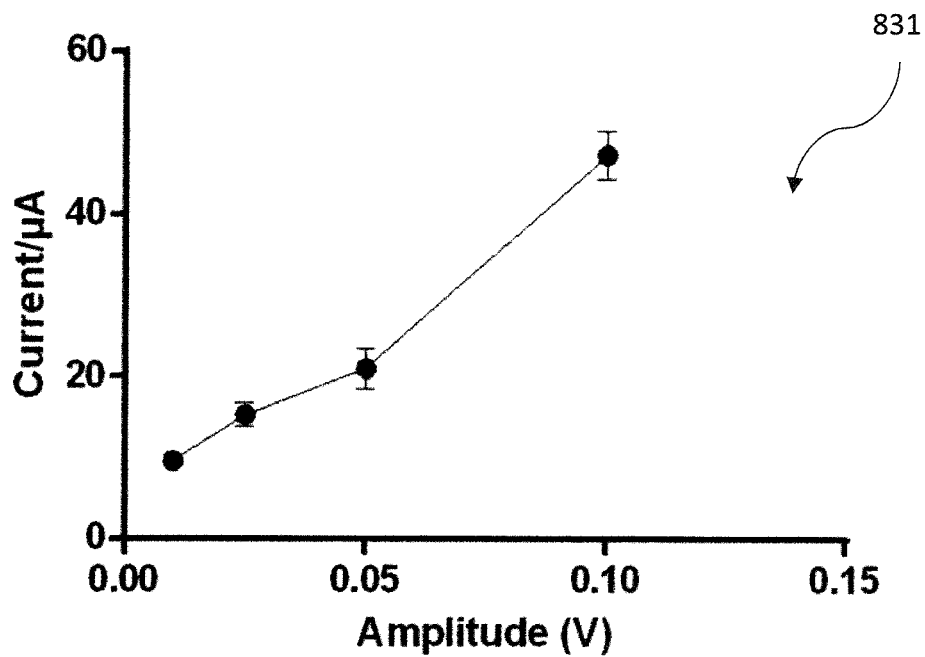
Figure 5C:
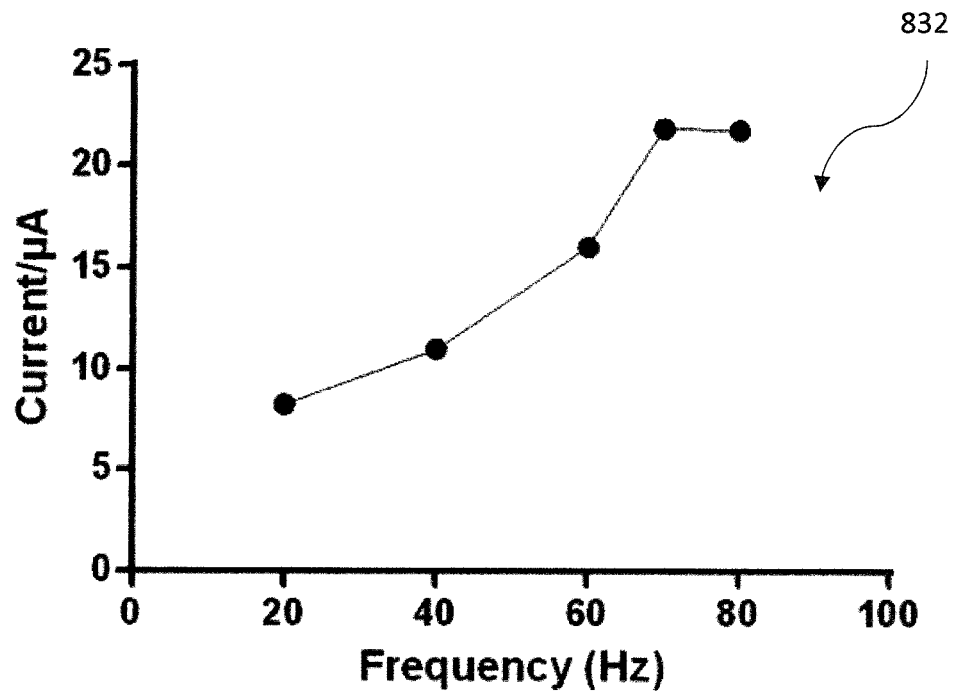
Figure 5D:
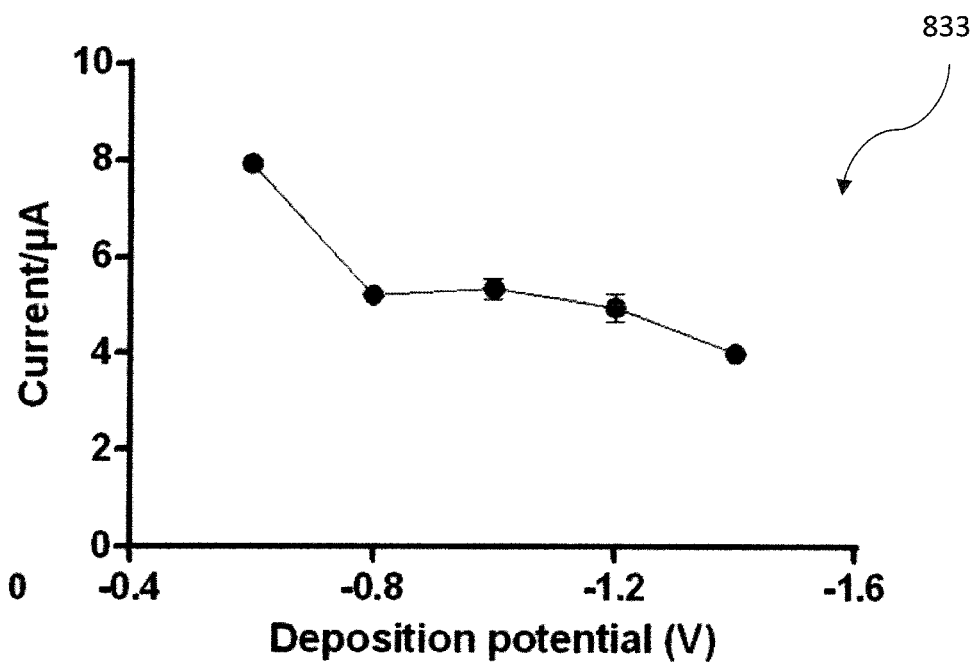

FIGS. 5A-5D include diagrams 830-833, which show effects of parameters on the stripping peak current of arsenic ion of the iron-chitosan microsensor, the sensor was fabricated by electroplating (100 $mA/cm^2$ of current density was used for deposition of the Fe-chitosan electroplating). The effect of different parameters (i.e. deposition potentials, deposition time and frequency) on the stripping peak current in a solution containing 10 ppb of $As^{3+}$ ions. A similar trend of deposition time was observed regarding iron/chitosan sensor compared to bismuth/chitosan. The frequency and amplitude have a significant effect on the stripping response (diagrams 831, 832: FIGS. 5B and 5C). The highest current of 47 µA of amplitude at 0.1 V and 23 µA of frequency at 80 Hz was showed, but the peak had an ambient noise due to amplitude property. Thus, 0.05 V of amplitude and 60 Hz of frequency was chosen to be the conditions for the iron/chitosan sensor.

Deposition potential is generally one of the critical parameters in stripping voltammetry. The currents for stripping of $As^{3+}$ at −0.6 V and above were lower than the ones obtained at −1.4 V. However, the evolution of hydrogen and oxygen at the working electrode at negative potentials more than −1.0 V reduced reproducibility of the measurements. −0.6 V was selected as an appropriate deposition potential, which provides the maximum $As^{3+}$ stripping peak current without hydrogen and oxygen interference.

Figure 6A:
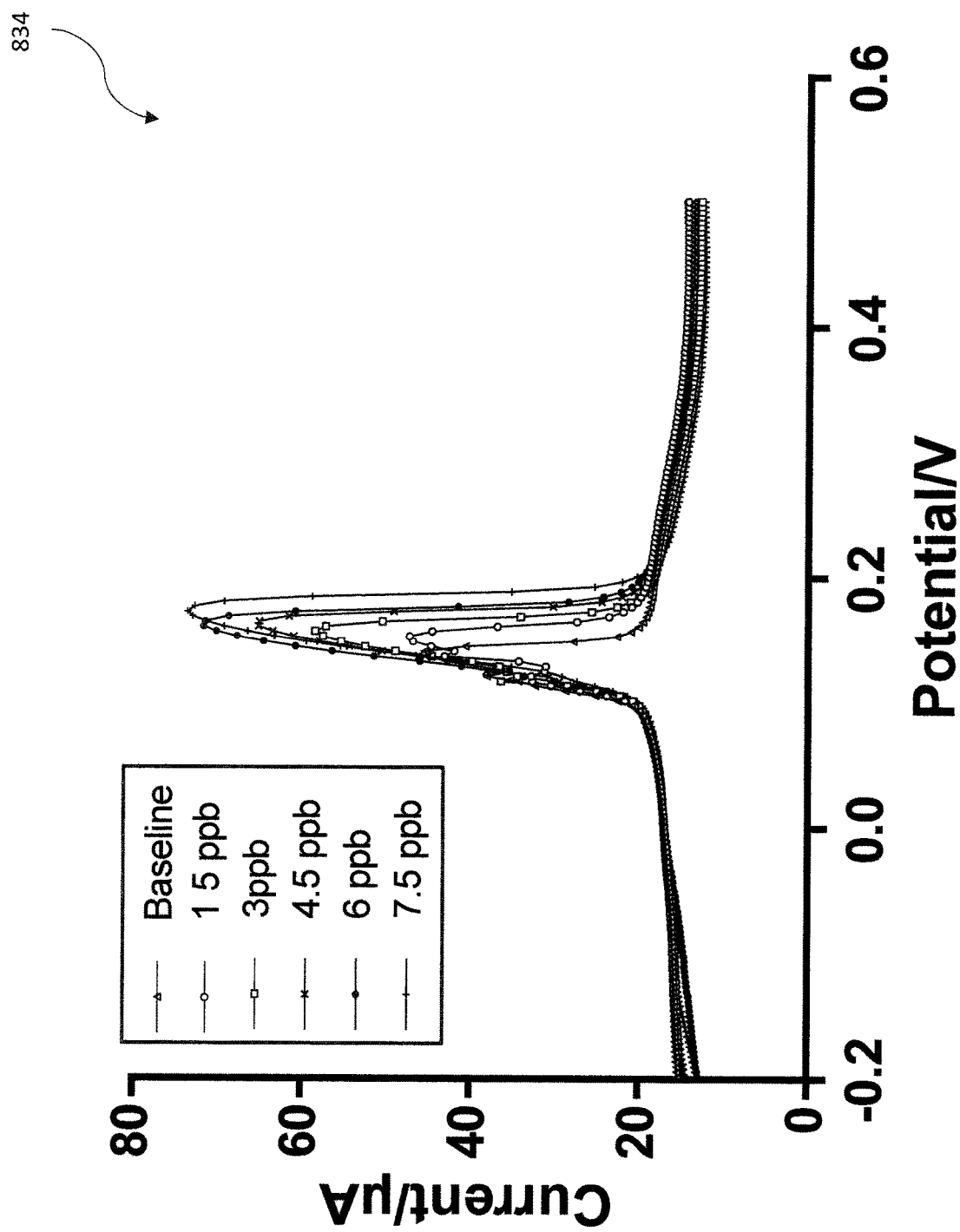
FIGS. 6A-6B are diagrams, respectively, of differential pulse SWASV and a corresponding calibration curve of $As^{3+}$ in 0.1 M acetate buffer at a pH of 4.5 during a method for making the sensor device, according to the present disclosure.
Figure 6B:
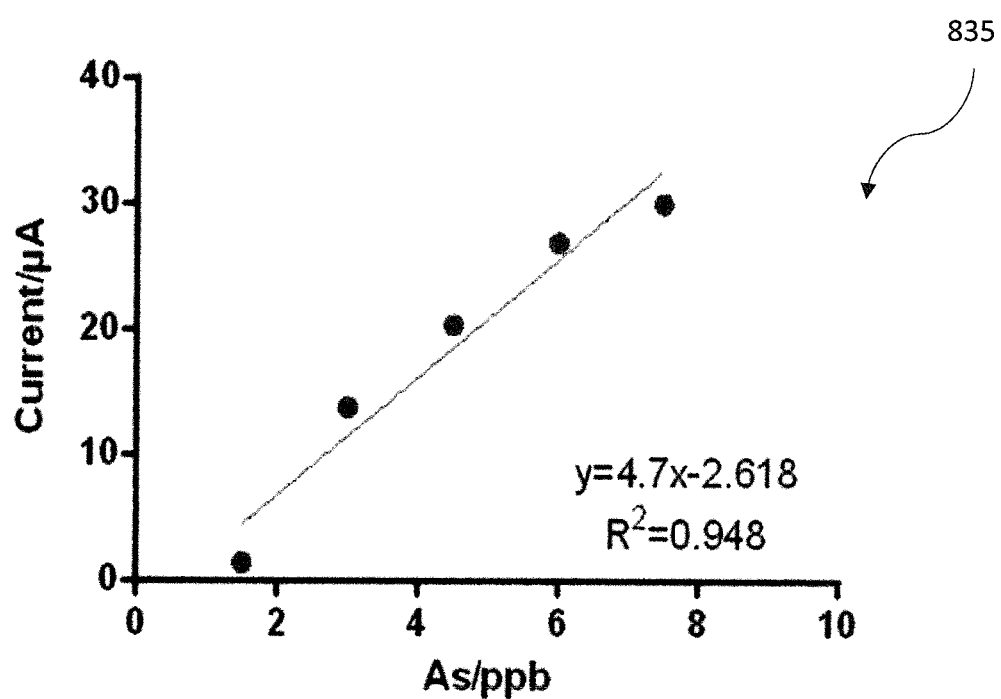
Figure 7:
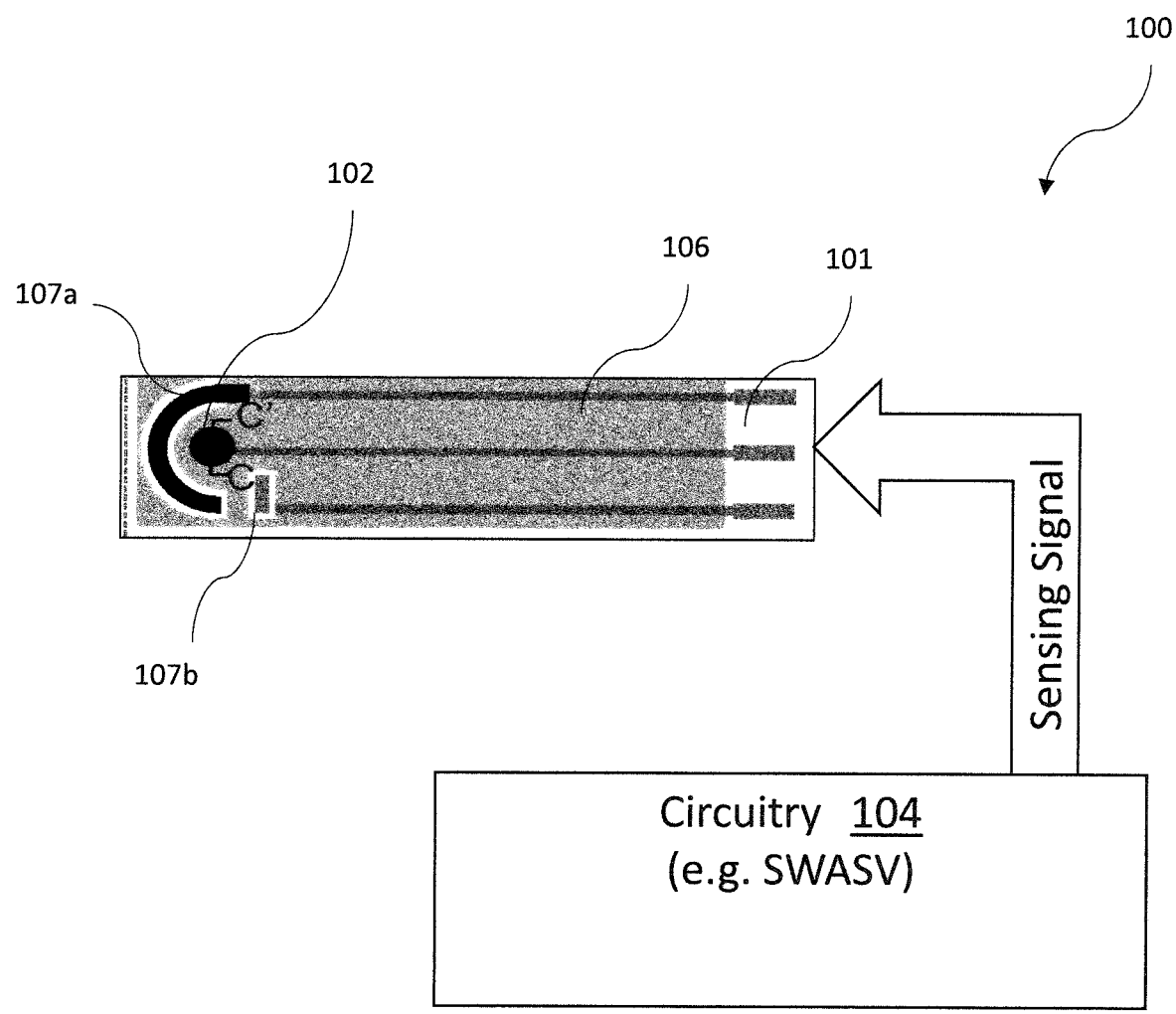
FIG. 7 is a schematic diagram of the sensor device, according an example embodiment of the present disclosure.

The SWASV responses of the iron-chitosan sensor to $As^{3+}$ ions were investigated in the range of 1.5 to 7.5 ppb under the conditions defined previously. The well-defined sharp peaks for $As^{3+}$ is located at 0.1 V. The correlations in the range of 1.5 to 7.5 ppb is: $I_p$=4.7x−2.618 (R2=0.948) and LOD was 1.5 ppb as shown in diagrams 834-835 of FIGS. 6A and 6B.

Conventional bulk sensors may be costly. The disclosed metal-biopolymer coated sensors can decrease the fabrication/production cost per sensor with improved sensitivity due to a synergetic effect of biopolymer on heavy metal holding. A disclosed metal-biopolymer coated sensor is expected to be manufactured at a cost of less $1. Uses for disclosed metal-biopolymer coated sensors include heavy metal ion detection in various water resources (city tap water and well water) and wastewater (industrial, municipal, and mining).

EXAMPLES

Disclosed embodiments of the invention are further illustrated by the following specific experimental examples, which should not be construed as limiting the scope or content of this present embodiments in any way.

To evaluate its accuracy in an example practical application, disclosed bismuth-chitosan and iron-chitosan composite-based sensors were used to the determine $Cd^{2+}$ and $Pb^{2+}$ and As3+ concentrations in real mining wastewater. The LOD in parts per billion (ppb) observed was 0.5 of $Cd^{2+}$, 1 of $Pb^{2+}$ and 3.75 of As in mining wastewater under bismuth/chitosan and Fe/chitosan sensor, respectively. The Relative Standard Deviation of Repeatability (RSD) percentage of the biopolymer coated carbon electrode for consecutive 8 measurements is 2.6% for $Cd^{2+}$ and 4.3% for $Pb^{2+}$, and 2.4% for $As^{3+}$ detection under 4 measurements, suggesting that coating material (e.g., bismuth and ferric) may have enhanced stability of electrodes for heavy metal ion detection in real wastewater.

The results of SWASV determination were compared to those obtained by $Cd^{2+}$, $Pb^{2+}$ and $As^{3+}$ using conventional inductively coupled plasma mass spectrometry (ICP-MS), shown in Table 1 below. It was found that the bismuth-chitosan and iron-chitosan did not have a strong impact on the interference under high dilution of heavy metal ions in mining water and it was possible to detect heavy metal ions in real-time. The appeal of the SWASV method using the bismuth-chitosan and iron-chitosan composite films for $Cd^{2+}$, $Pb^{2+}$ and $As^{3+}$ analysis is its simplicity and rapidity.

TABLE 1

Performance of bismuth/chitosan sensor in mining wastewater applications

| Mining wastewater | Limits of detection (ppb) | Reproducibility (n) | Relative standard deviation (%) | bismuth/chitosan Sensor | Fe/chitosan Sensor (ppb) | ICP-MS | Recovery (%) |
|---|---|---|---|---|---|---|---|
| $Cd^{2+}$ | 0.5 | 8 | 2.6 | 106.7 ± 2.1 | | 100 | 106 |
| $Pb^{2+}$ | 1 | 8 | 4.3 | 76.2 ± 4.1 | | 70 | 108.8 |
| $As^{3+}$ | 3.75 | 4 | 2.4 | | 292.7 ± 4.1 | 300 | 97.5 |

Referring now to FIGS. 7 and 8A-8F, a sensor device 100 for detecting metal is now described. As noted above, the sensor device 100 may be used for in situ detection of metals in fluids (e.g. water). The sensor device 100 illustratively comprises a substrate 101, an electrode 102 on the substrate, and a biopolymer-metal composite film 103 on the electrode. For example, the substrate 101 may comprise a dielectric material, such as a polymer plastic material.

The biopolymer-metal composite film 103 comprises a metal and a biopolymer. In some embodiments, the biopolymer comprises one or more of a polysaccharide material, a chitosan material, and a chitin material. The metal may comprise one or more of iron, copper, and bismuth, for example. The biopolymer-metal composite film 103 may comprise a thin film composite having a thickness in the range of 0.1-20 μm.

The sensor device 100 illustratively includes circuitry 104 coupled to the electrode 102 and configured to apply a sensing signal to the electrode. In the illustrated embodiment, the electrode 102 comprises a single electrode. In other embodiments, the electrode 102 may comprise a plurality of electrodes.

Figure 8A:
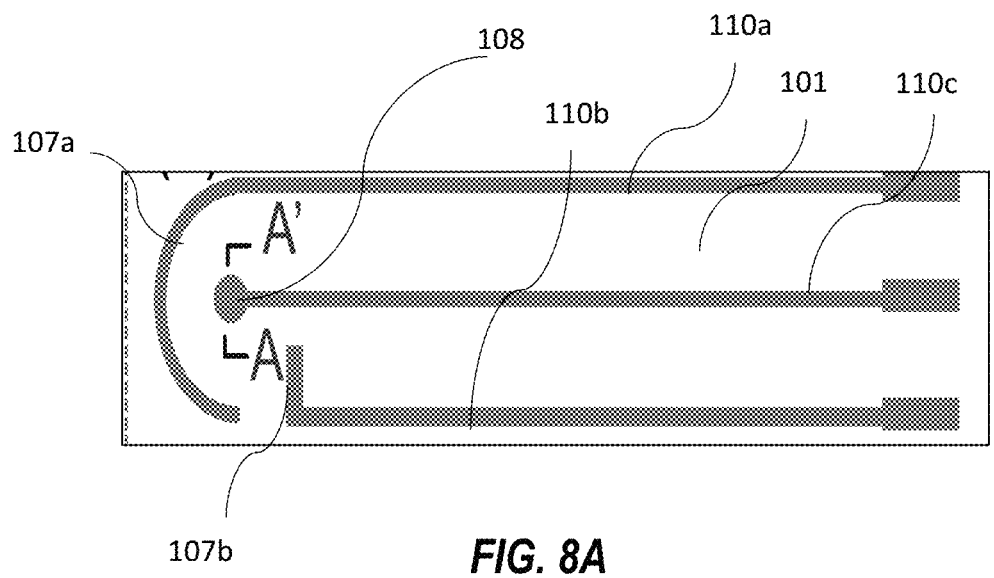
FIGS. 8A-8F are schematic diagrams of the sensor device of FIG. 7 during manufacture.
Figure 8B:
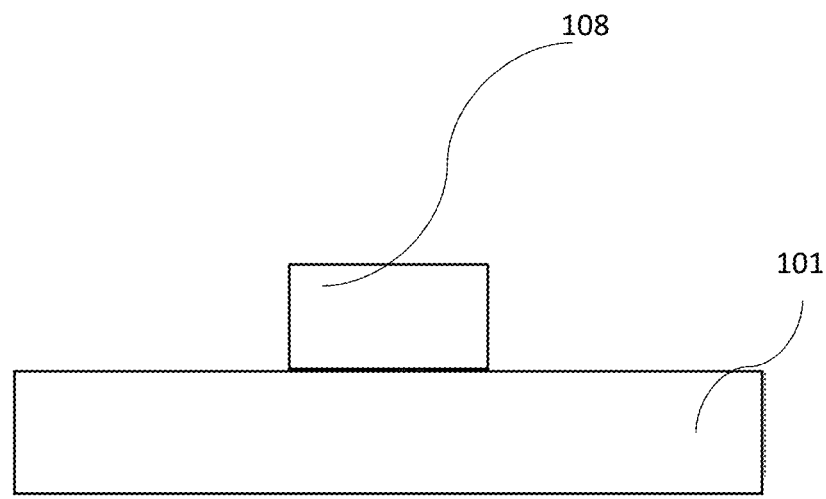
Figure 8C:
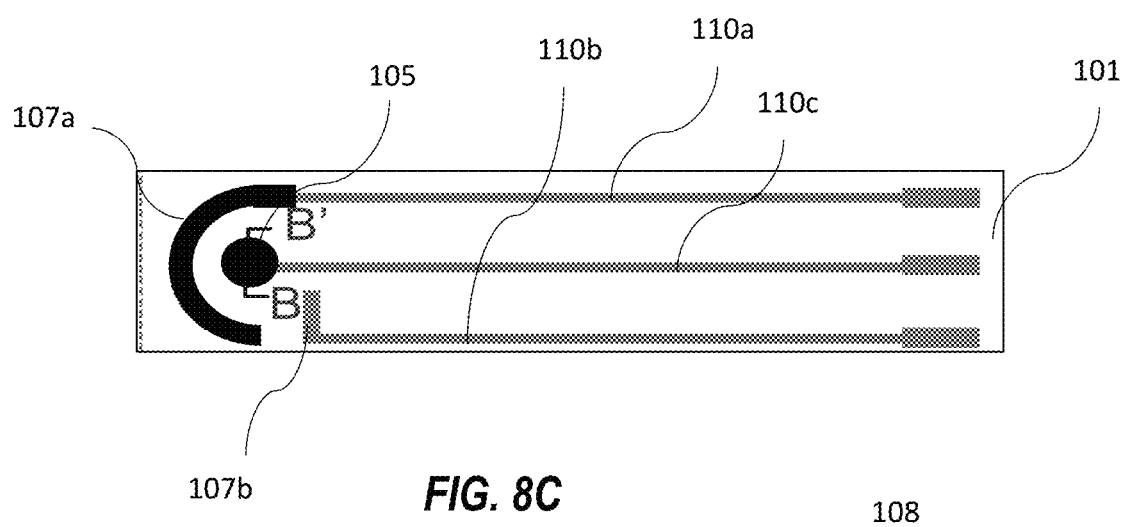
Figure 8D:
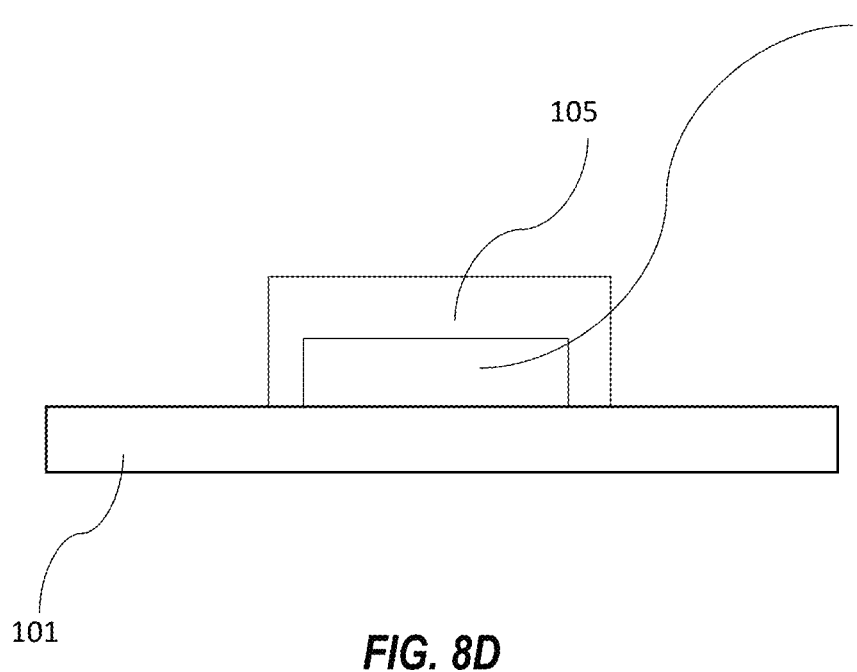
Figure 8E:
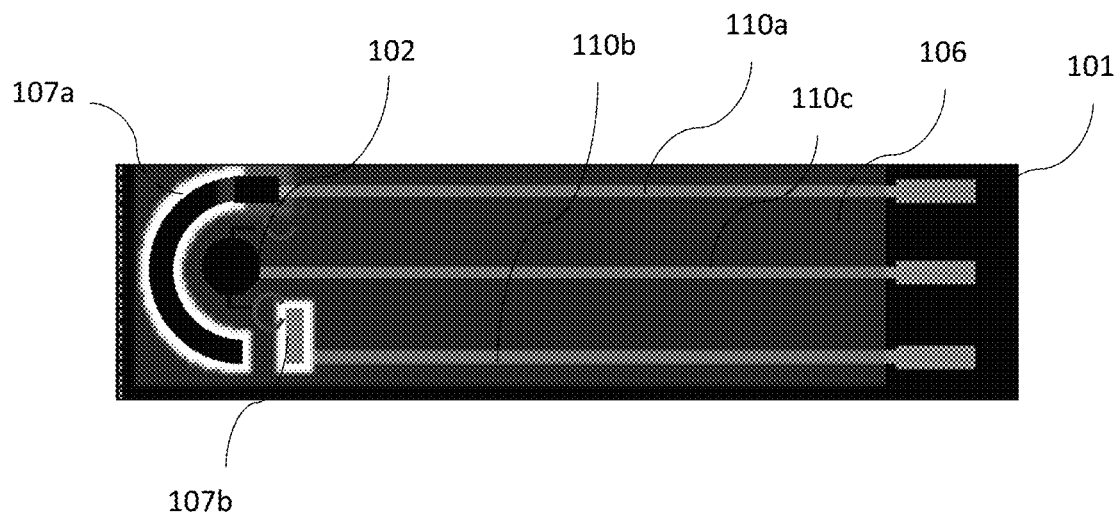
Figure 8F:
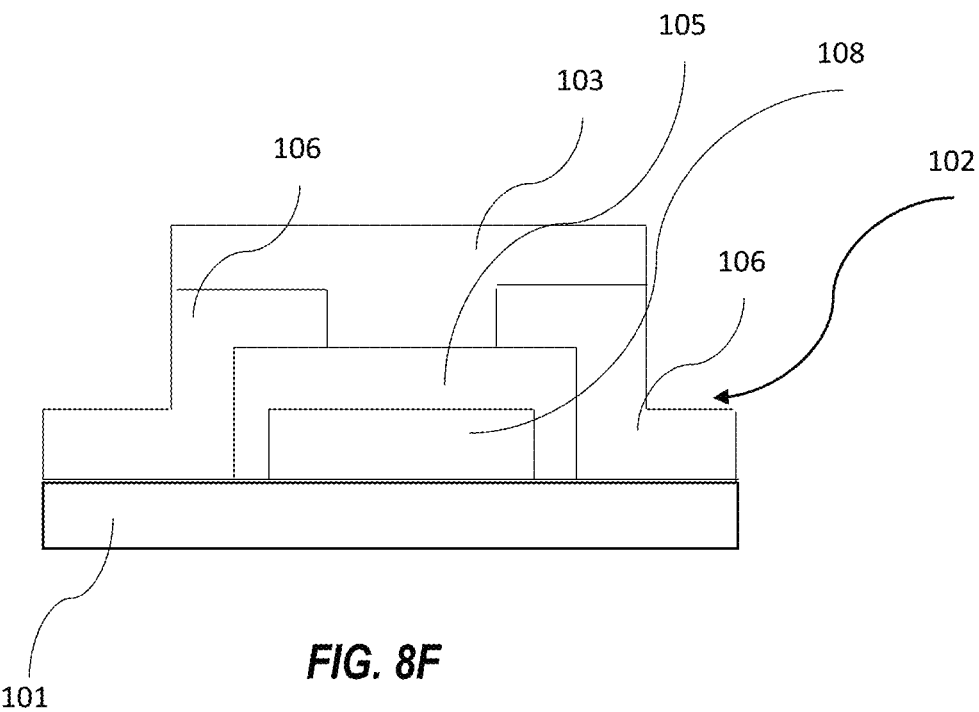
Figure 9:
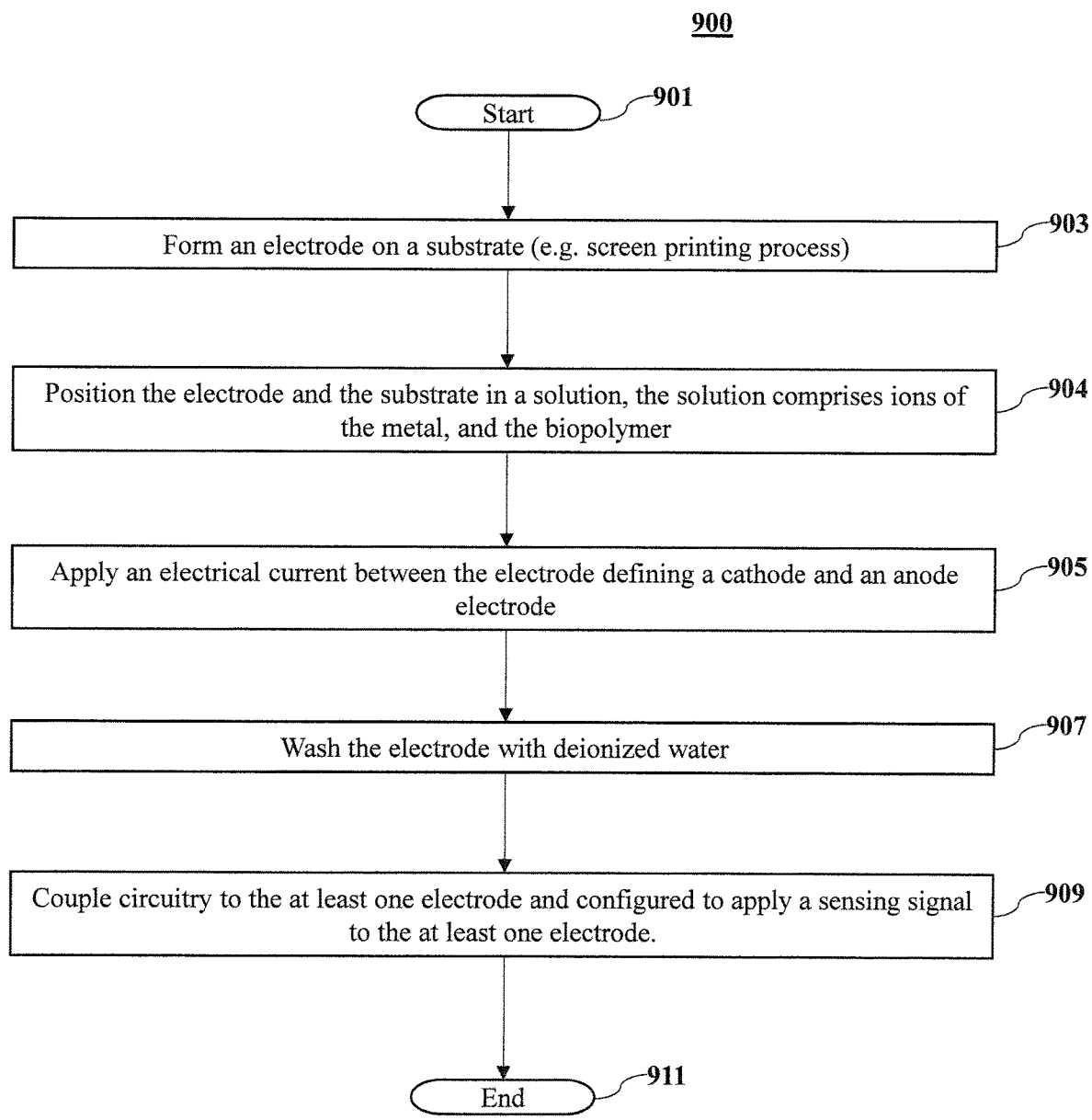
FIG. 9 is a flowchart illustrating a method for making the sensor device of FIGS. 8A-8D, according to an example embodiment of the present disclosure.

As perhaps best seen in FIG. 8F, the electrode 102 illustratively includes a multi-layer electrode. The multi-layer electrode 102 comprises an electrically conductive layer 108 (e.g. silver, copper, gold, aluminum) on the substrate 101, an electrode layer 105 (e.g. silicon dioxide, polymer dielectric) on the electrically conductive layer, and an insulator layer 106 over the electrically conductive layer. For example, the electrode layer 105 may comprise one or more of carbon and gold.

The sensor device 100 illustratively comprises a counter electrode 107a, and a reference electrode 107b. The counter electrode 107a illustratively comprises an electrically conductive base layer (e.g. silver, copper, gold, aluminum), and a cover layer over the electrically conductive base layer, the cover layer including carbon. The reference electrode 107b may comprise an electrically conductive base layer (e.g. silver, copper, gold, aluminum), and a cover layer over the electrically conductive base layer, the cover layer comprise one or more of silver, and silver chloride. In some embodiments, the circuitry 104 is configured to generate the sensing signal to comprise a plurality of SWASV sensing signals.

As will be appreciated by those skilled in the art, the plurality of SWASV sensing signals is applied to the electrode 102, the counter electrode 107a, and the reference electrode 107b. Advantageously, the sensor device 100 may provide a high number of SWASV sensing operations during a lifetime.

The sensor device 100 illustratively comprises first, second, and third electrically conductive traces 110a-110c respectively coupled on their first ends to the counter electrode 107a, the reference electrode 107b, and the electrode 102. The sensor device 100 illustratively comprises first, second, and third contact pads coupled to second ends of the first, second, and third electrically conductive traces 110a-110c.

Referring now to FIGS. 2, 8A-8F, and 9, a method for making the sensor device 100 is now described, which begins at Block 901 in flowchart 900. The method illustratively comprises forming an electrode 102 on a substrate 101. For example, the forming of the electrode 102 may include a screen printing process, a sputtering process, or a deposition process. (Block 903).

The method illustratively includes forming a biopolymer-metal composite film 103 on the electrode 102. (Blocks 904, 905, 907). The biopolymer-metal composite film 103 includes a metal and a biopolymer.

In an example embodiment depicted in a diagram 810 of FIG. 2, the forming of the biopolymer-metal composite film 103 on the electrode 102 illustratively includes an electrodeposition process (i.e. co-electrodeposition process). The electrodeposition process includes generating the biopolymer-metal solution (e.g., the illustrated chitosan/$Bi^{3+}$). (Blocks 811-813). In this illustrative example, chitosan powder is stirred at 60° C. with acetate acid to produce a chitosan solution. (Blocks 811-812). The chitosan solution is combined with bismuth(III) nitrate to produce a chitosan/$Bi^{3+}$ solution. (Block 813).

The electrodeposition process includes positioning the electrode 102 and the substrate 101 in a solution. (Blocks 814-815, 904). The solution comprise ions of the metal, and the biopolymer. The electrodeposition process includes applying an electrical current between the electrode 102 defining a cathode and an anode electrode (i.e. the illustrated counter electrode 107a). (Block 905).

The method illustratively comprises coupling circuitry 104 to the electrode 102. (Blocks 909, 911). The circuitry 104 is configured to apply a sensing signal to the electrode 102. The method concludes at Block 911.

In the following, an exemplary discussion of an example embodiment of the sensor device is now provided.

INTRODUCTION

Water and soil contamination by heavy metals has gained much attention due to its significant impact on public health. Heavy metal ions (e.g., zinc, copper, cadmium and lead) are used in several industrial applications and are recognized as agents that present various toxic effects to humans, animals and other living organisms. These metals are well-known water pollutants, which are not biodegradable, and have long biological half-lives; hence, they tend to bio-accumulate in higher trophic levels of the food chain. Due to growing rigorous environmental regulations, the legal limits for heavy metals in drinking water (e.g., 5 ppm of zinc [$Zn^{2+}$] and 0.015 ppm of lead [$Pb^{2+}$]) is becoming stricter [1]. Particularly, $Pb^{2+}$ leaching from galvanic corrosion and elevation of lead levels in household plumbing systems have increasingly drawn public attention [2]. The lead in drinking water has been regulated by Lead and Copper Rule (LCR) with the permissible $Pb^{2+}$ concentration less than 15 ppb [3] and thus fast and simple detection of lead in drinking water is imperative for public health.

Among currently available analytical methods, environmental monitoring systems based on electrochemistry are considered complementary to the traditional techniques (e.g., Inductively coupled plasma (ICP) and Atomic absorption spectroscopy (AAS)), promising inexpensive and portable instruments [4, 5]. Particularly, square-wave anodic stripping voltammetry (SWASV) based on metallic mercury (Hg) has been well-defined for heavy metal detection. However, due to the toxicity of Hg, environmentally benign materials that can replace Hg for heavy metal sensing materials are highly sought after. One of the most well-studied electrode materials is bismuth due to its ability to form alloys with various heavy metals, wide potential window applicable to electrochemical detection, and low toxicity [6]. Despite the excellent compatibility of bismuth, when fabricating microsensors using bismuth, the brittleness and detachment still impose practical problems for industrial applications [7].

Chitosan is a biopolymer [8] that can form stable chelates with many transition metal ions through its hydroxyl and amino groups. This characteristic can be exploited for the development of electroanalytical procedures to detect heavy metal ions where chitosan is employed as an electrode modifier to adsorb metals ions and improve the sensitivity [9-12]. Furthermore, the useful characteristics of chitosan in terms of electrochemistry for the design of modified electrodes include biocompatibility, a high mechanical strength, good adhesion on traditional electrochemical surfaces, and a relatively low cost, as it is from a renewable resource [13-15]. Chitosan films have been deposited by an ex-situ plating method, particularly, on glassy carbon [16] and screen-printed ink [17], which have been mostly studied due to their high surface to volume ratio, high electron mobility and compatibility to stripping voltammetry for heavy metal detection. However, only single ion detection (primarily $Pb^{2+}$) has been tested and multi heavy metal ions detection was not fully explored. In addition, the sensor performance in terms of real-time and in situ heavy metal detection for effective monitoring and managements of water systems still needs to be studied for field applications [18].

Materials and Methods

A. Preparation of Biopolymer-Coated Electrode

Figure 10A:
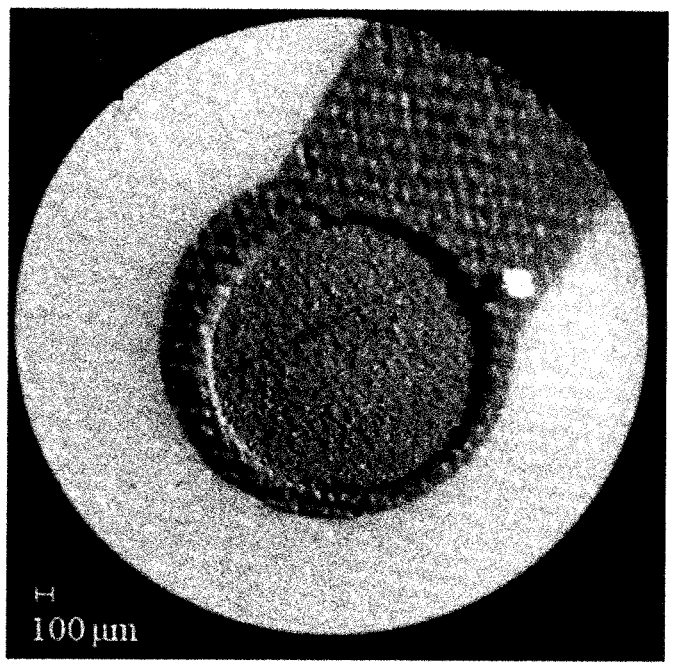
FIGS. 10A-10B are microscopic images of an example embodiment of the electrode from the sensor device before and after formation of the biopolymer-metal composite film, respectively.
Figure 10B:
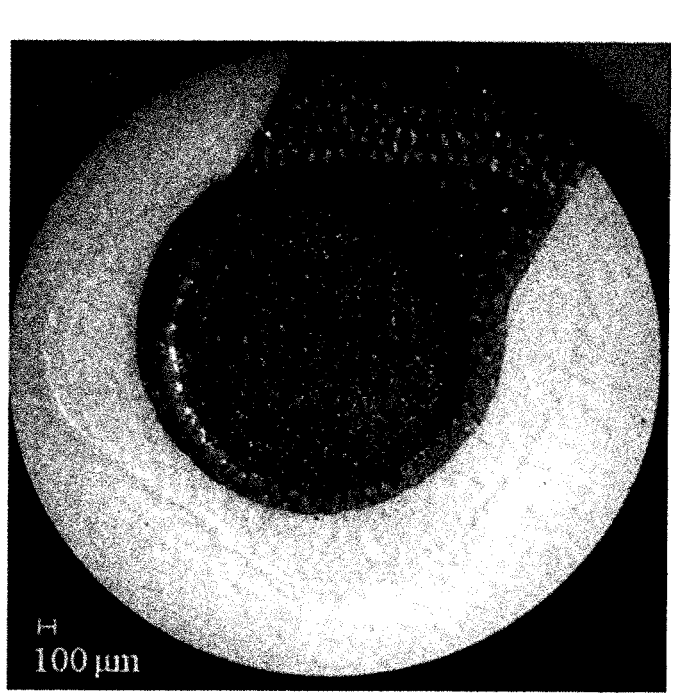

A screen-printed carbon electrode with a 2-mm diameter (RRPE1001C, as available from Pine Instrument Company of Grove City, Pa.) was used as a base (substrate) working electrode. A biopolymer solution was prepared by dissolving 24 mg chitosan in 20 mL of 0.1M acetic acid solution (pH 4.5) and stirred using a magnetic stirrer at 700 rpm for 24 hrs. Then, 5 μL of 0.78 mM chitosan solution was drop casted over the working electrode and completely dried by a heat gun for 4 min. The drop casting and drying process was repeated 4 times which was determined from our preliminary test. Then, the biopolymer-coated carbon electrode was tested using cyclic voltammetry (CV) to confirm the electrochemical properties. The CV scan was performed between −1.2 and 0.0 V at a rate of 50 mV/s using a potentiostat (PalmSens3, as available from PalmSens Compact Electrochemical Interfaces from BASi Corporation of West Lafayette, Ind.). The surface morphology of the biopolymer-coated electrode was investigated under a microscopic observation (Revelation III DIN, Microscope, as available from LW scientific, Inc., Lawrenceville, Ga.). The images 836, 837 are shown in FIGS. 10A-10B (Microscopy images (×400) of chitosan on a modified carbon electrode: image 836 before versus image 837 after chitosan biopolymer coating).

B. Sample Preparation

Analytical grade Lead (II) nitrate and Zinc (II) chloride (Sigma-Aldrich) were used without further purification. A 0.1 M acetate buffer (pH 4.6), prepared by mixing appropriate amounts of acetic acid and sodium acetate, was used to prepare solutions of the supporting electrolyte. The stock solutions of 0.1 M $Pb^{2+}$ and $Zn^{2+}$ were prepared by dissolving the appropriate amount of lead (II) nitrate and Zinc (II) chloride in deionized (DI) water. The real mining wastewater and extraction leachate of heavy metal contaminated soil were obtained Il-gang mine and Yong-san industrial estate in South Korea. All experiments were conducted at room temperature (23° C.) with a relative humidity of 45%.

C. SWASV Procedure

Figures 11A, 11B:
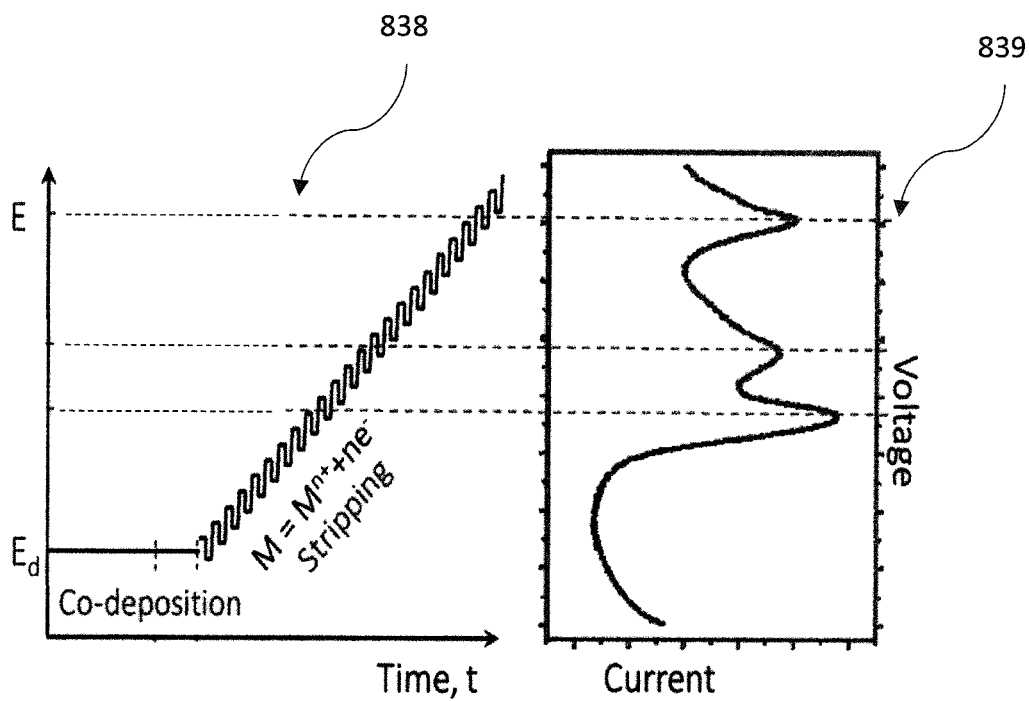
FIGS. 11A and 11B are diagrams of a SWASV waveform for a three-electrode system illustrating deposition and stripping potentials with time and a voltammogram during a stripping step in an example embodiment of the sensor device, respectively, according to the present disclosure.

Sensor performance was tested in an electrochemical cell (e.g., Compact Voltammetry Cell-Starter Kit, as available from Pine Instrument Company of Grove City, Pa.). The developed biopolymer-coated carbon electrode was used as a working electrode, a co-planar carbon electrode was used as a counter electrode (e.g., RRPE1001C, as available from Pine Instrument Company of Grove City, Pa.), and a separate Ag/AgCl electrode filled with 3 M KCl (e.g., MI-401, as available from Microelectrodes, Inc., Bedford, N.H.) was used as a reference electrode. The electrochemical cell included a generic mini-USB connector to banana jack cell cables, a cell cap and a cell grip. FIGS. 11A-11B include a diagram 838 of a SWASV waveform illustrating deposition and stripping potentials with time and a diagram 839 of a voltammogram during a stripping step.

First, $Pb^{2+}$ and $Zn^{2+}$ were deposited at −1.2 V vs. Ag/AgCl for 300 s, unless specified otherwise, in 0.1 M acetate buffer (pH 4.6) containing $Pb^{2+}$ and $Zn^{2+}$. After the deposition step, the reduced metals were stripped off by SWASV with step potential of 4 mV, amplitude of 50 mV, and frequency of 20 Hz. The stripping potential was applied in the range of −1.2 V to 0 V. A cleaning step was performed prior to ex-situ electrodeposition by biasing the working electrode at +0.2 V for 30 s. A PalmSens EIS (as available from PalmSens Compact Electrochemical Interfaces from BAST Corporation of West Lafayette, Ind.) was used as a potentiostat for all experiments. All data are expressed as the mean±standard deviation (SD) unless indicated otherwise.

D. Materials Characterization

Figure 12:
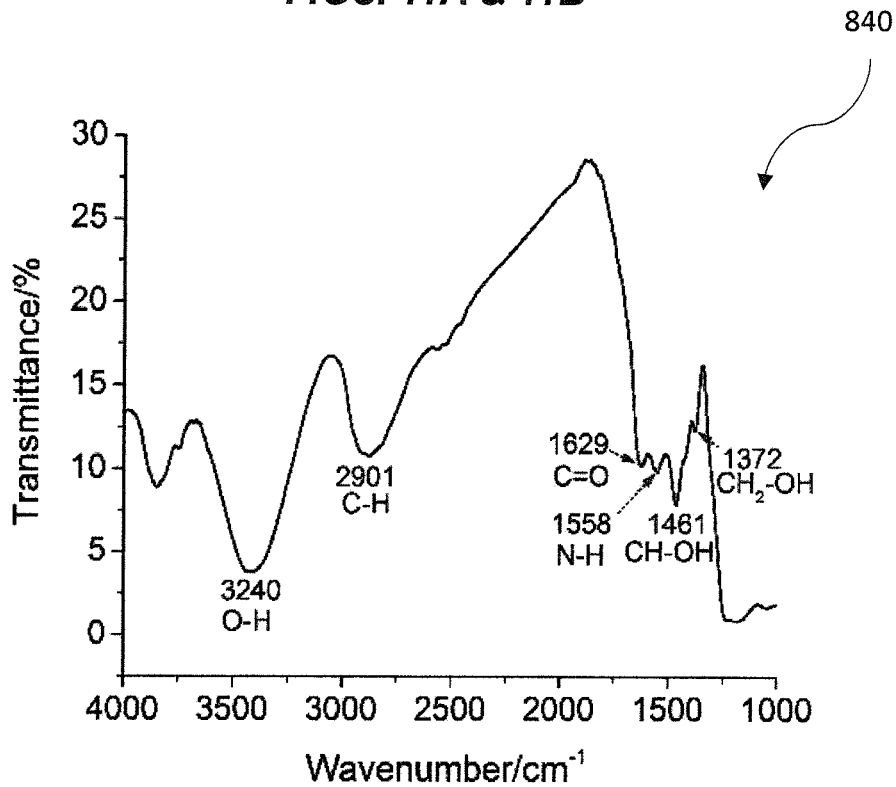
FIG. 12 is a diagram of a Fourier-transform infrared spectroscopy (FTIR) spectrum of chitosan deposited on the carbon electrode in 4000 $cm^{-1}$ to 1000 $cm^{-1}$ range in an example embodiment of the sensor device, according to the present disclosure.

FTIR spectra were obtained using a Vector-22 FTIR spectrometer (as available from Bruker Corporation of Billerica, Mass.) in the range of 4000 $cm^{-1}$ to 1000 $cm^{-1}$ at a resolution of 2 $cm^{-1}$. The FTIR spectrum of the chitosan deposited carbon electrode in diagram 840 of FIG. 12 showed the important peaks to identify functional groups. The oscillation of O—H and C—H is observed at 3420 $cm^{-1}$ and 2901 $cm^{-1}$, respectively. Similarly, stretching vibration of C=O and N—H of the sample is observed at 1629 $cm^{-1}$ and 1558 $cm^{-1}$, respectively. In the wave number range, 1300 $cm^{-1}$ to 1500 $cm^{-1}$, two oscillation characteristics were observed at 1461 $cm^{-1}$ and 1372 $cm^{-1}$ which represent CH—OH and $CH_2$—OH, respectively. The presence of O—H, C—H, C=O, N—H, CH—OH, and $CH_2$—OH functional groups in the fabricated electrode shows that chitosan was effectively deposited on the carbon electrode [19].

Results and Discussion

Figure 13A:
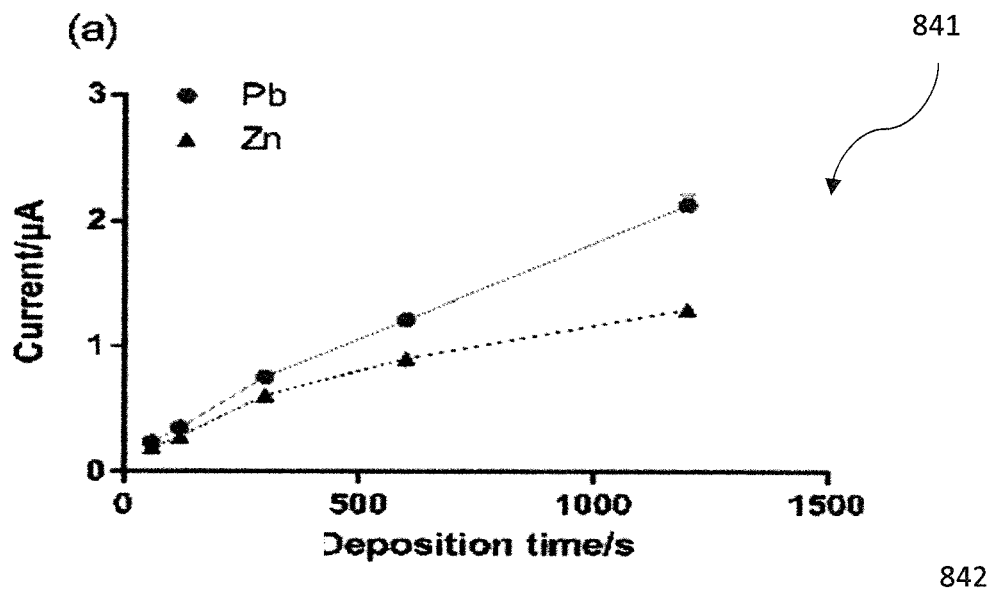
FIGS. 13A, 13B, and 13C are diagrams of deposition time, amplitude, and frequency on the stripping peak currents of $Zn^{2+}$ and $Pb^{2+}$ of the biopolymer-coated carbon electrode in an example embodiment of the sensor device, respectively, according to the present disclosure.
Figure 13B:
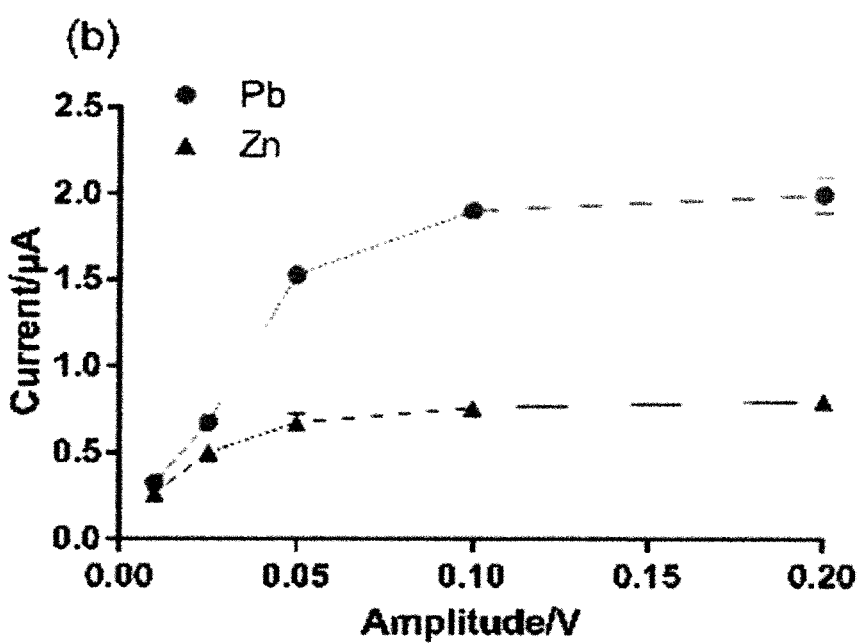

A. Optimization of Biopolymer-Coated Carbon Electrode Working Parameters for Detection of Heavy Metal In order to determine optimal current outputs and peak shapes for detecting $Zn^{2+}$ and $Pb^{2+}$ ions by SWASV, the developed electrodes were tested under different operational conditions which include: varying deposition time, amplitude and frequency for initial deposition of heavy metal ions on the electrode. FIGS. 13A-13B shows the influence of deposition time (diagram 841), amplitude (diagram 842), and frequency (diagram 843) on the stripping peak of $Zn^{2+}$ and $Pb^{2+}$ using the chitosan-coated carbon electrode. Experimentally defined −1.2 and +0.0 V were used as deposition and cleaning potentials, respectively. The peak currents of $Zn^{2+}$ and $Pb^{2+}$ increased linearly from 0.19±0.03 and 0.21±0.02 to 1.31±0.04 and 2.13±0.06 μA with prolonged deposition time, respectively. Although the sensitivity was improved with longer deposition time, it also reduced the upper detection limit due to the surface saturation at high metal ion concentrations [20]. The peak current for $Zn^{2+}$ initially increased with deposition time, then slightly increased after 300 s probably due to the saturation of $Zn^{2+}$ on the electrode surface (diagram 341: FIG. 13A). In the case of $Pb^{2+}$, a linear correlation between peak currents and deposition time until 1500 s was observed. Thus, 300 s was chosen to be the optimal and practical co-deposition time for $Zn^{2+}$ and $Pb^{2+}$ measurements.

Figure 13C:
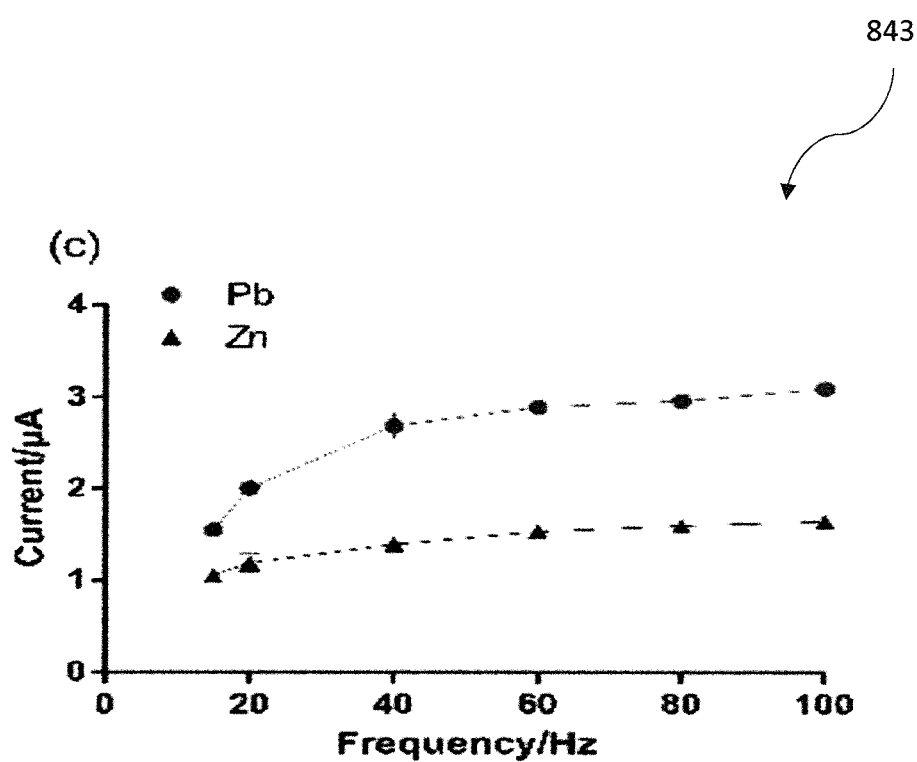

The amplitude and frequency showed significant effects on the stripping response (diagrams 842-843: FIGS. 13B and 13C). The highest current was observed using 0.1 V amplitude and a 40 Hz frequency; however, the peaks had ambient noise under those conditions due to amplitude and frequency properties of vibration [21]. Finally, 0.05 V of pulse amplitude and 20 Hz of frequency were selected for further evaluation of the biopolymer-coated sensor performance for in situ $Zn^{2+}$ and $Pb^{2+}$ detection.

B. Detection of Heavy Metals by SWASV

Figure 14A:
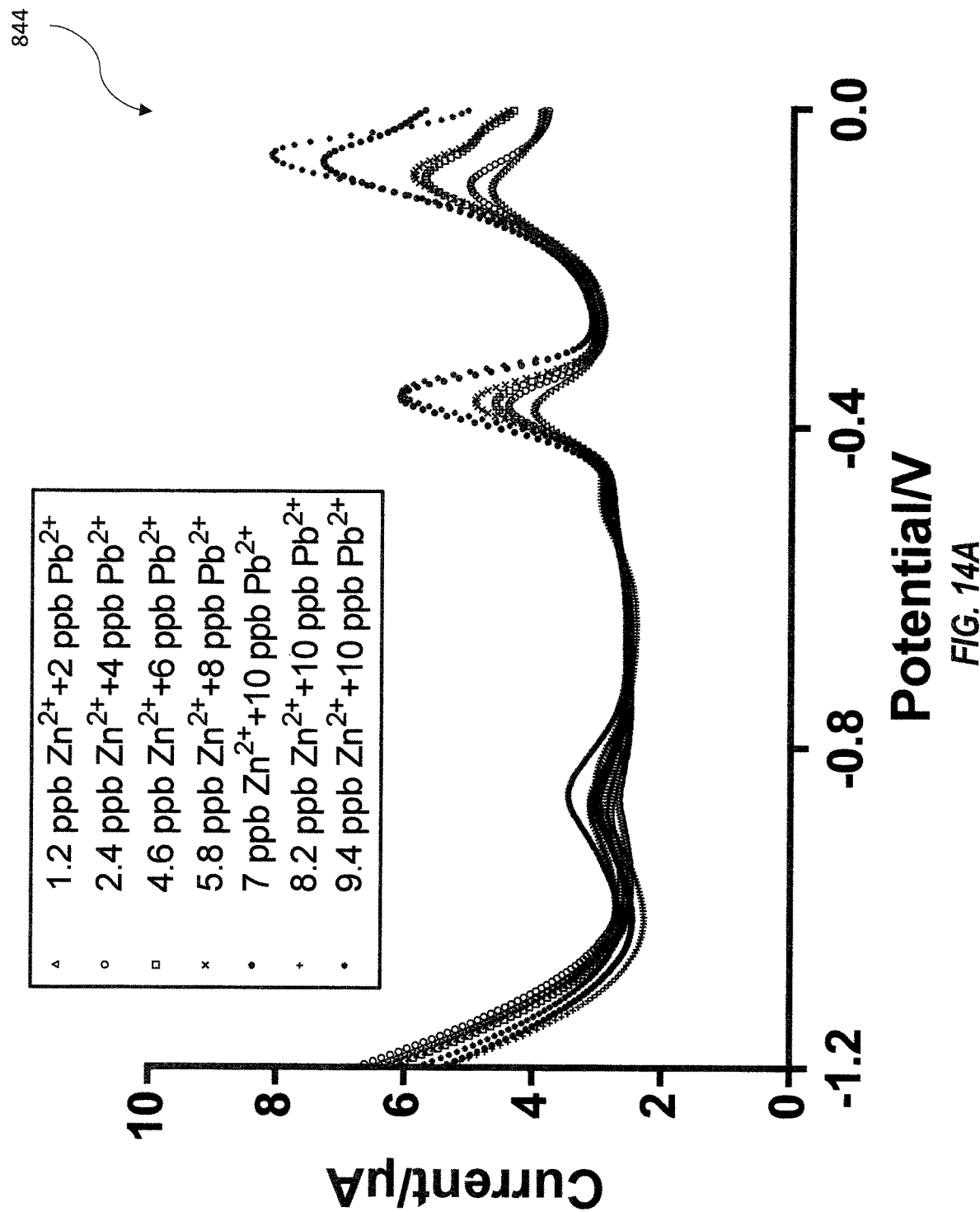
FIGS. 14A and 14B are diagrams of SWASV and corresponding calibration curves, respectively, of $Zn^{2+}$ and $Pb^{2+}$ in an example embodiment of the sensor device, according to the present disclosure.
Figure 14B:
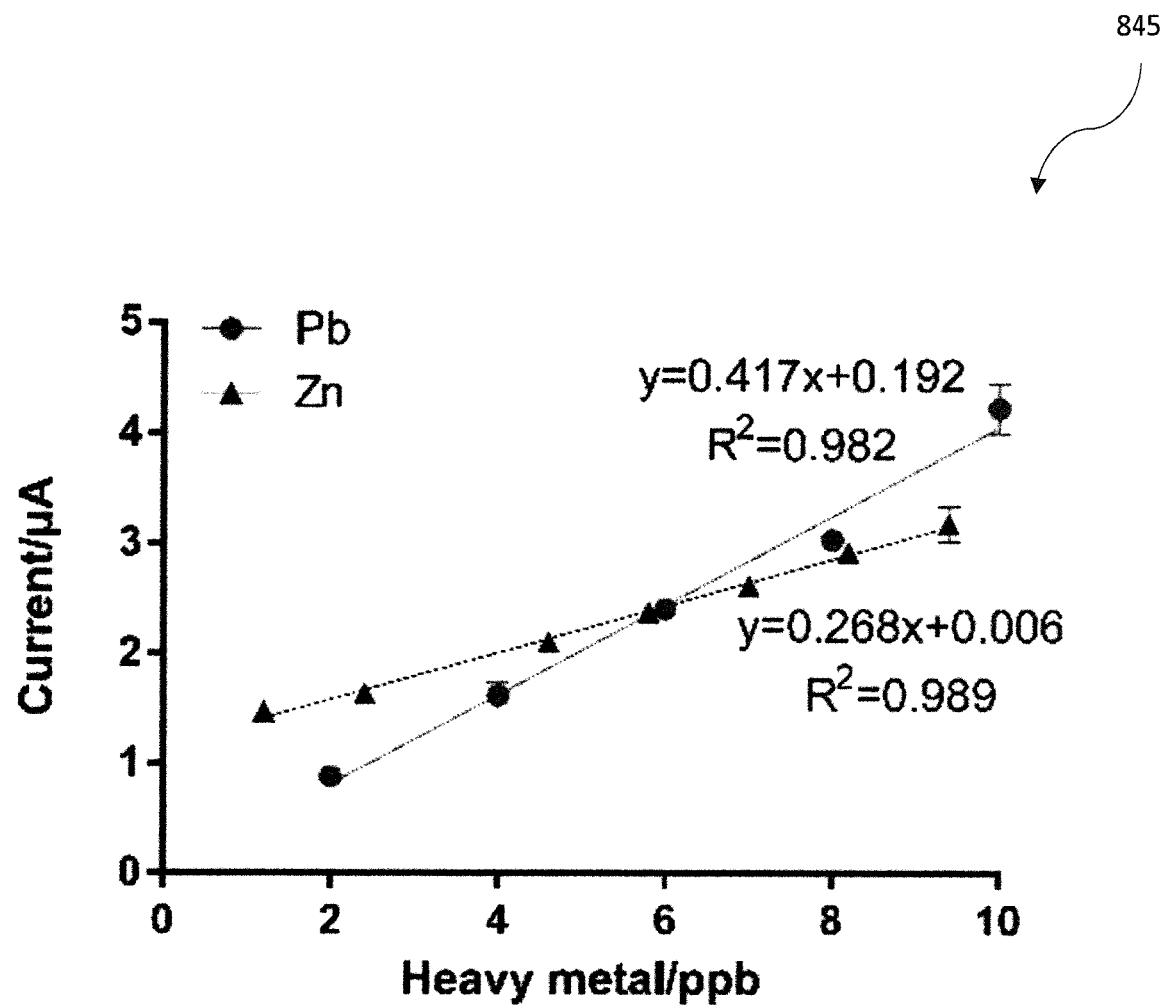

The preliminary test on the detection range of the $Zn^{2+}$ and $Pb^{2+}$ using the developed biopolymer-coated carbon electrode showed the measurement ranges up to 200 ppb for $Zn^{2+}$ and 500 ppb for $Pb^{2+}$, respectively. However, for improving the sensor accuracy in simultaneous heavy metal detection, the analytical performance was evaluated in the lower range between 1 and 10 ppb in a 0.1 M acetate buffer solution. The SWASV responses (diagrams 844, 845) for different concentrations of heavy metal ions are illustrated in FIGS. 14A-14B. In particular, differential pulses are shown for SWASV (diagram 844) and corresponding calibration curves (diagram 845) of Zn2+ and Pb2+ in 0.1 M acetate buffer (pH 4.6). Deposition time is 300 s with a −1.2V deposition potential, 0.004 V potential step, 0.05 V amplitude, and 20 Hz frequency.

Deposition time was 300 s with a −1.2V deposition potential, 0.004 V potential step, 0.025 V amplitude, and 20 Hz frequency. The hydrogen evolution potential and the electrode oxidation potential were observed throughout the applied stripping potentials. The electrolytic hydrogen evolution at around −1.0V and the oxidation of the chitosan electrode at about −0.2 V was determined as shown in FIGS. 14A-14B. The well-defined sharp peaks for $Zn^{2+}$ and $Pb^{2+}$ are located at ca. −0.86 and −0.37V, respectively, (FIGS. 14A-14B) and the peak currents were proportionally increased with positive shifts of peak potentials as the concentration of heavy metal ions increase. The SWASV peak currents were obtained with correction to the base line and then the calibration plots were evaluated from the peak currents. The corresponding calibration plots and correlation coefficients are y=0.268x+0.006 and $R^2$=0.989 for $Zn^{2+}$, y=0.417x+0.192 and $R^2$=0.982 for $Pb^{2+}$ (x: concentration (ppb), y: current (μA)), based on three times of the background noise (S/N=3). LOD were calculated based on the method by Lee et al [22] using calibration curves. LOD was determined to be 0.6 ppb for $Zn^{2+}$ and 1.0 ppb for $Pb^{2+}$ for simultaneous analysis. Compared to a screen-printed bare carbon electrode (using, e.g., RRPE1001C, as available from Pine Instrument Company of Grove City, Pa.) without chitosan coating (LOD: 2-4 ppm), the chitosan biopolymer-coated planar carbon electrode showed greater improvement of LOD (2,000-4,000 times) in $Pb^{2+}$ detection.

Table 2 shows the comparison of the developed biopolymer-coated carbon electrodes with other formerly reported polymer-modified electrodes. The results show that the developed biopolymer-coated carbon electrode using chitosan exhibits an excellent and reliable performance for simultaneous determination of two heavy metal ions compared to limited, single heavy metal detection done by others. This demonstrates the applicability of biopolymer-coated carbon electrode to multiple heavy metal detection in cost-effective manners without using a bulk electrode or Bismuth modification.

TABLE 2

Comparison of heavy metal detection between the developed biopolymer-coated carbon electrodes and other materials previously reported.

| Electrode substrate | Measurement technique | Detection limit (ppb) $Zn^{2+}$ | Detection limit (ppb) $Pb^{2+}$ | Reproducibility (n) | RSD (%) | Ref. |
|---|---|---|---|---|---|---|
| chitosan/carbon nanotubes film electrodes | SWASV | — | 500 | — | — | [16] |
| chitosan-modified screen-printed carbon electrode | DPASV | — | 0.03 | 15 | 7 | [17] |
| chitosan-modified glassy carbon electrode | DPV | — | 60 | 10 | 3.5 | [23] |
| chitosan-coated screen-printed carbon electrode | SWASV | 1.2 | 1 | 30 | 4.8 ($Zn^{2+}$) 5.4 ($Pb^{2+}$) | This study |

C. Reproducibility of the Biopolymer-Coated Electrode

Figure 15:
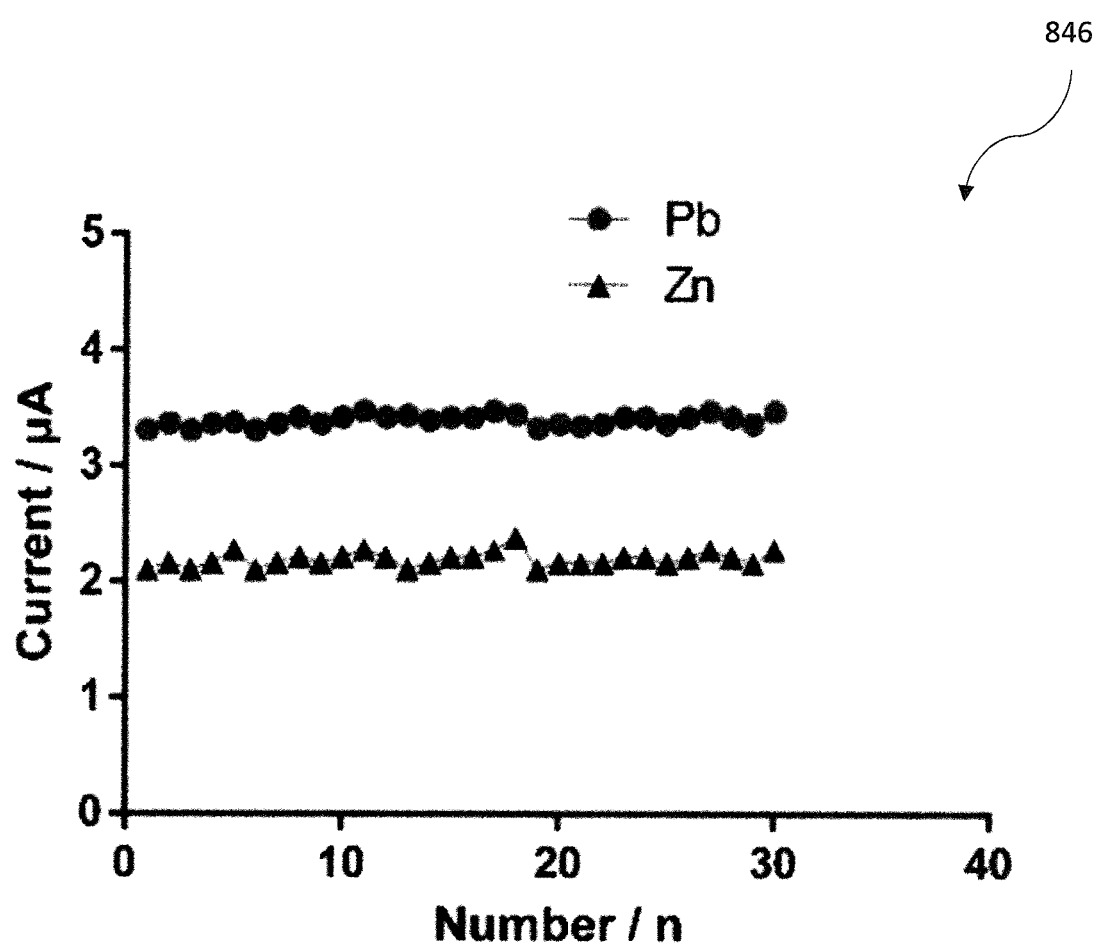
FIG. 15 is a diagram of reproducibility of $Zn^2$ and $Pb^{2+}$ detection using the chitosan-coated carbon electrode in an example embodiment of the sensor device, according to the present disclosure.

A series of repetitive SWASV response measurements for 10 ppb of $Zn^{2+}$ and $Pb^{2+}$ ions in a 0.1 M acetate buffer solution were performed to further evaluate the stability of the biopolymer-coated carbon electrode. SWASV parameters were 300 s of deposition time, −1.2V of deposition potential, 0.004 V of potential step, 0.05 V of amplitude, and 20 Hz of frequency. The biopolymer-coated electrode displayed an excellent relative standard deviation (RSD) and reproducibility compared to previous studies (Table 2). In the previous reports, which used chitosan-coated electrodes [17, 23], the successive measurements with the same electrodes was limited to 15 times when differential pulse anodic stripping voltammetry (DPASV) was used. However, in this study, 30 successive measurements with a stable peak current at 300 s deposition time were recorded by the present biopolymer coated electrode using SWASV (diagram 846: FIG. 15; The reproducibility of $Zn^{2+}$ and $Pb^{2+}$ detection using the chitosan-coated carbon electrode. Both $Zn^{2+}$ and $Pb^{2+}$ concentration was 10 ppb.). Highly reproducible stripping currents were observed, with a RSD of 4.8% for $Zn^{2+}$ and 5.4% for $Pb^{2+}$. Therefore, the biopolymer-coated electrode has demonstrated an excellent stability for repetitive SWASV measurements.

D. Application to a Tap Water and Real Wastewater Environment

Figure 16A:
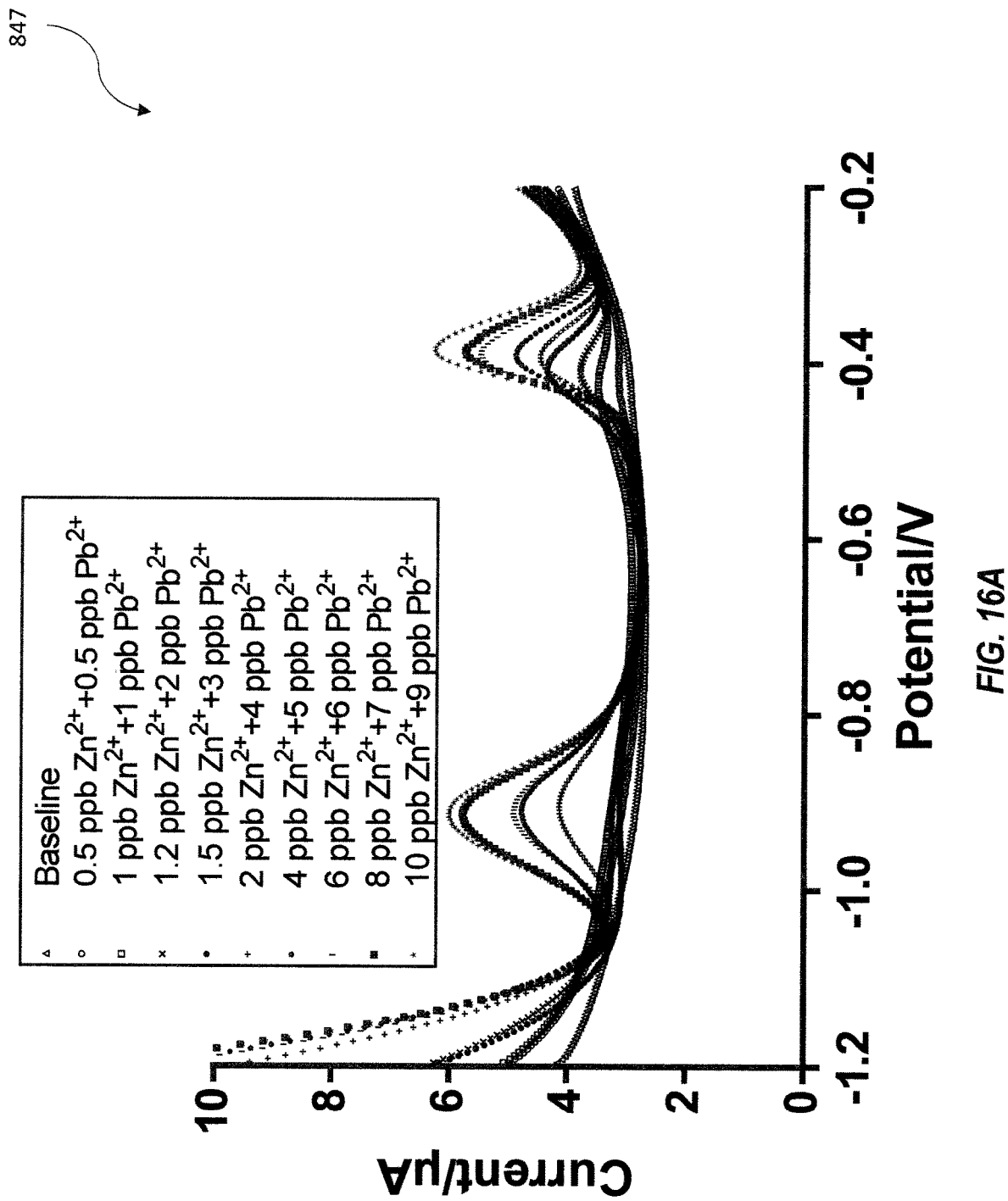
FIG. 16A is a diagram of simultaneous detection of $Zn^{2+}$ and $Pb^{2+}$ in a tap water environment with SWASV using a biopolymer-coated carbon electrode in an example embodiment of the sensor device, according to the present disclosure.
Figure 16B:
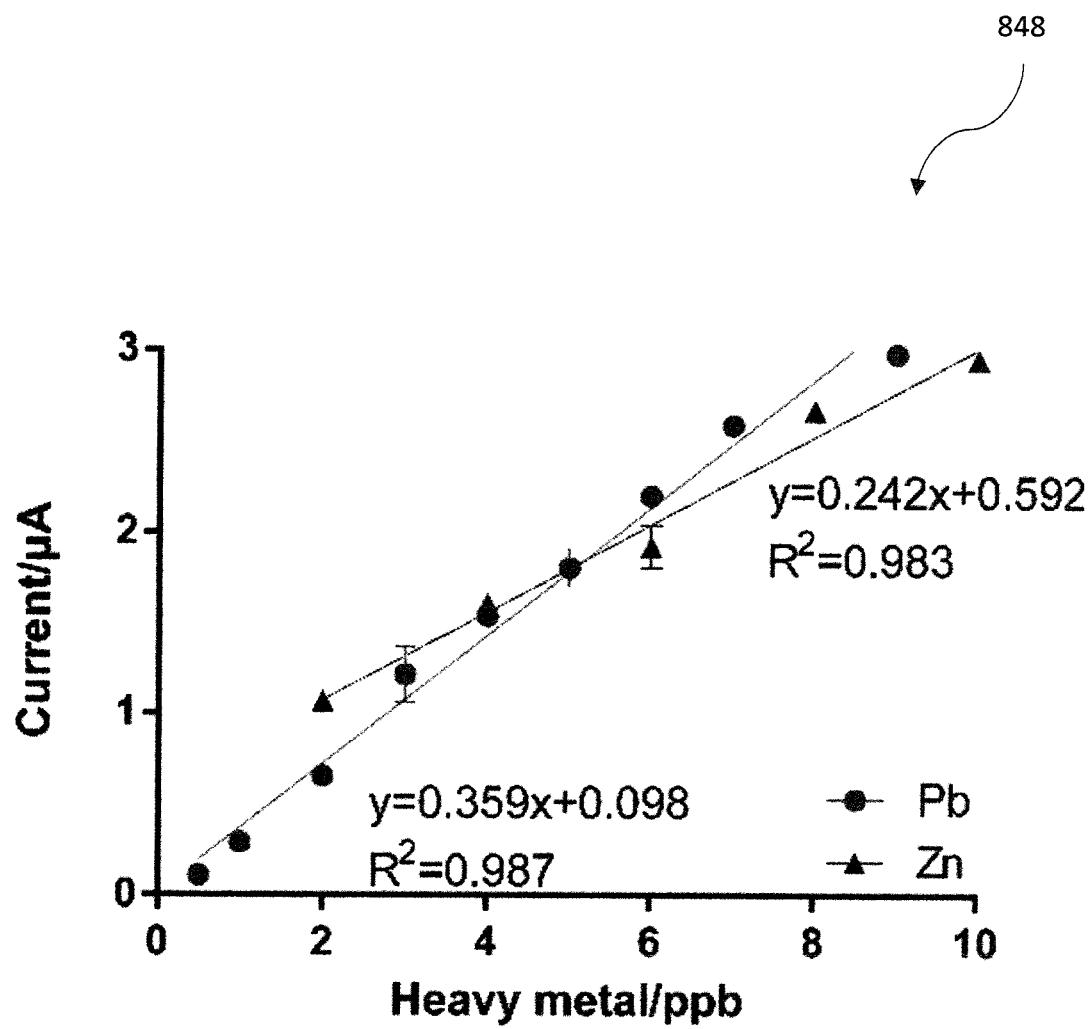
FIG. 16B is a diagram of calibration curves with error bars for $Zn^{2+}$ and $Pb^{2+}$ for simultaneous detection of Zn and $Pb^{2+}$ in a tap water environment in an example embodiment of the sensor device, according to the present disclosure.

The sensor reliability was examined by applying the pre-defined SWASV method for simultaneous measurements of $Zn^{2+}$ and $Pb^{2+}$ in a prepared drinking water using a local tap-water in which a certain amount of $Zn^{2+}$ and $Pb^{2+}$ were added (2 to 10 ppb for $Zn^{2+}$ and 0.5 to 10 ppb for $Pb^{2+}$) (diagrams 847, 848: FIGS. 16A-16B; simultaneous detection of $Zn^{2+}$ and $Pb^{2+}$ in a tap water environment: diagram 847 shows SWASV using a biopolymer-coated carbon electrode in a 0.1 M acetate buffer solution (pH 4.6) (background solution was tap-water), and diagram 848 shows calibration curves with error bars for $Zn^{2+}$ and $Pb^{2+}$).

A $Zn^{2+}$ peak could not be obtained for concentrations lower than 2 ppb which may be attributed to the proximity of its stripping peak to the hydrogen evolution background current and/or to a low Zn deposition efficiency (e.g., lower diffusivity of $Zn^{2+}$ compared to $Pb^{2+}$) in water samples [24]. However, the slopes of the standard addition curves were 0.242 µA/µM of $Zn^{2+}$ and 0.359 µA/µM of $Pb^{2+}$ (the range of the spiked concentrations were 2 to 10 ppb for $Zn^{2+}$ and 0.5 to 10 ppb for $Pb^{2+}$) with correlation coefficients 0.983 and 0.987 under the measurement conditions found with the proposed method (SWASV, 300 s deposition time with a −1.2V deposition potential, 0.004 V potential step, 0.05 V amplitude, and 20 Hz frequency). The application results showed that the biopolymer-coated carbon electrode is reliable and suitable for sensitive and selective determination in situ of $Zn^{2+}$ and $Pb^{2+}$ in a real water environment.

Figure 17A:
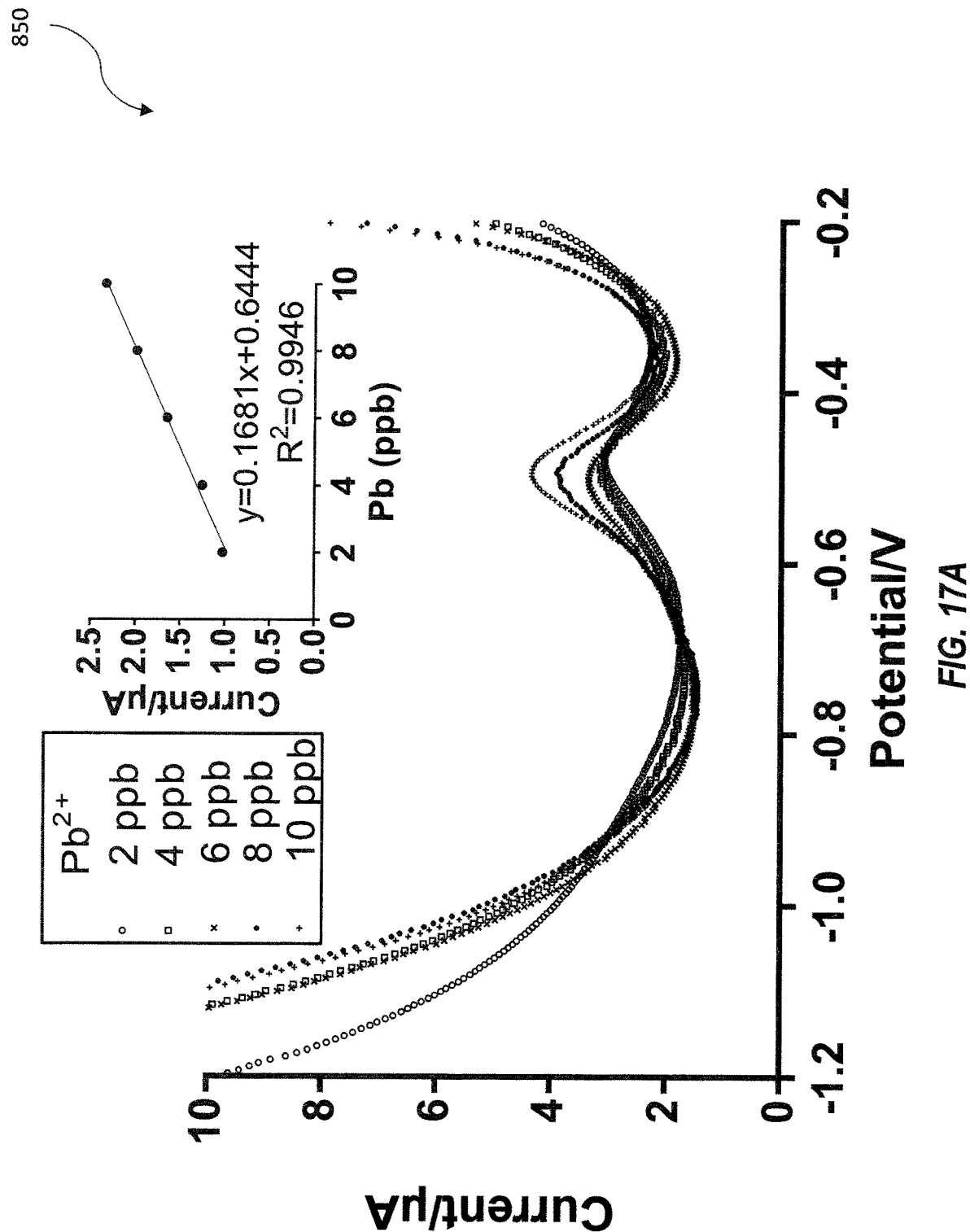
FIGS. 17A and 17B are diagrams of simultaneous detection of $Zn^{2+}$ and $Pb^{2+}$ in mine wastewater and soil wastewater, respectively, using an example embodiment of the sensor device, according to the present disclosure.
Figure 17B:
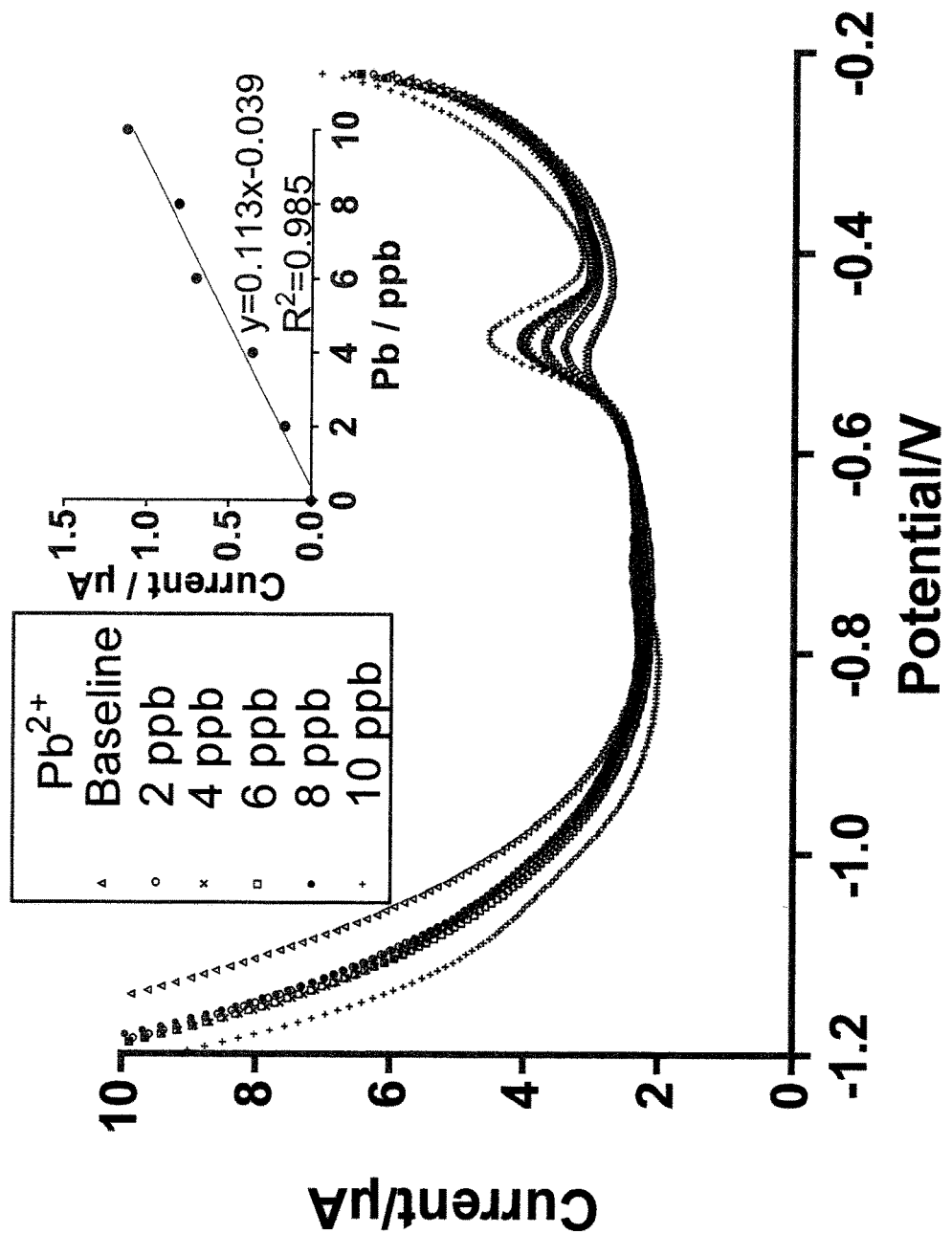

To evaluate sensor performance in a real wastewater environment, the biopolymer-coated sensor was tested for the determination of $Pb^{2+}$ in mining wastewater and extraction leachate of heavy metal contaminated soil. First, pre- and post-calibration curves were constructed using the same wastewater by spiking various concentrations of $Pb^{2+}$ between 0 and 2 ppb to the diluted mining wastewater sample and soil leachate sample (diagrams 850, 851: FIGS. 17A-17B; simultaneous detection of $Zn^{2+}$ and $Pb^{2+}$ in a real heavy metal environment: diagram 850 shows mine wastewater, and diagram 851 shows soil waste). The concentrations of $Pb^{2+}$ in the wastewater samples were then determined in several times (Table 3). The results of SWASV determination of $Pb^{2+}$ in the samples were validated using AAS. A relative standard deviation (RSD) and recovery were 4.3% and 108.8% for the mining wastewater and 13.7% and 96% for the soil leachate, respectively, indicating that the developed biopolymer-coated sensor displayed acceptable reproducibility in real environmental samples containing heavy metals. However, the developed sensor showed limitation of $Zn^{2+}$ detection in the wastewater samples probably due to the presence of $Cu^{2+}$ within the samples (e.g., 10.5 ppm for mining wastewater and 38.1 ppm for soil leachate). It is well known that the Cu—Zn intermetallic species, which develop during the deposition step, can interfere with sensor performance [25].

TABLE 3

Heavy metal detection in real environmental samples and sensor performance validation

| Sample | LOD (ppb) $Zn^{2+}$ | LOD (ppb) $Pb^{2+}$ | No. of measurements (n) | RSD (%) | Validation This study | Validation AAS* | Recovery (%) |
|---|---|---|---|---|---|---|---|
| Mining wastewater | — | 1 | 8 | 4.3 | 76.2 ± 4.1 ppb | 67 ± 0.9 ppb | 108.8 |
| Soil leachate | — | 1 | 3 | 13.7 | 1632 ± 12 ppm | 1640 ± 16 ppm | 96 |

*Atomic absorption spectroscopy

CONCLUSION

Biopolymer-coated carbon electrodes were successfully applied for in situ determination of heavy metals using SWASV. The proposed method was able to detect both $Zn^{2+}$ and $Pb^{2+}$ simultaneously with good sensitivity and detection limit. The RSD of the biopolymer coated carbon electrode for consecutive 30 measurements is 4.8% for $Zn^{2+}$ and 5.4% for $Pb^{2+}$ detection, suggesting that biopolymer may have enhanced stability of electrodes for heavy metal ion detection compared to a bare carbon electrode. Using tap water, mining wastewater, and soil leachate samples in which dissolved organic carbon (DOC) and various ionic species are present, the developed biopolymer coated carbon electrode was successfully tested for the detection of heavy metals. The overall results demonstrate that, with its simplicity and rapidity of the measurement, the biopolymer-coated planar screen-printed carbon electrode is applicable to in situ heavy metal analysis in water or on contaminated sites without the need for sample transportation to the laboratory or complex sample preparation steps.

Many modifications and other embodiments of the present disclosure will come to the mind of one skilled in the art having the benefit of the teachings presented in the foregoing descriptions and the associated drawings. Therefore, it is understood that the present disclosure is not to be limited to the specific embodiments disclosed, and that modifications and embodiments are intended to be included within the scope of the appended claims.

REFERENCES (THE CONTENTS OF WHICH ARE HEREBY INCORPORATED BY REFERENCE IN THEIR ENTIRETY)

[1] S. D. Richardson, "Disinfection by-products and other emerging contaminants in drinking water," TrAC Trends in Analytical Chemistry, vol. 22, no. 10, pp. 666-684, 2003.

[2] M. Edwards, S. Triantafyllidou, and D. Best, "Elevated blood lead in young children due to lead-contaminated drinking water: Washington, D C, 2001-2004," Environmental science & technology, vol. 43, no. 5, pp. 1618-1623, 2009.

[3] USEPA, "40 CFR Part 141 Subpart I—Control of Lead and Copper" National Primary Drinking Water Regulations, 2012.

[4] S.-Y. Liu et al., "Innovative solid-state microelectrode for nitrite determination in a nitrifying granule," Environmental science & technology, vol. 42, no. 12, pp. 4467-4471, 2008.

[5] S. Silva, C. Alves, S. Muchado, L. Mazo, and L. Avaca, "Electrochemical determination of nitrites in natural waters with ultramicroelectrodes," Electroanalysis, vol. 8, no. 11, pp. 1055-1059, 1996.

[6] J. Wang, J. Lu, S. B. Hocevar, P. A. Farias, and B. Ogorevc, "Bismuth-coated carbon electrodes for anodic stripping voltammetry," Analytical chemistry, vol. 72, no. 14, pp. 3218-3222, 2000.

[7] G.-H. Hwang, W.-K. Han, J.-S. Park, and S.-G. Kang, "An electrochemical sensor based on the reduction of screen-printed bismuth oxide for the determination of trace lead and cadmium," Sensors and Actuators B: Chemical, vol. 135, no. 1, pp. 309-316, 2008.

[8] A. Varma, S. Deshpande, and J. Kennedy, "Metal complexation by chitosan and its derivatives: a review," Carbohydrate Polymers, vol. 55, no. 1, pp. 77-93, 2004.

[9] F. C. Vicentini, T. A. Silva, A. Pellatieri, B. C. Janegitz, O. Fatibello-Filho, and R. C. Faria, "Pb (II) determination in natural water using a carbon nanotubes paste electrode modified with crosslinked chitosan," Microchemical Journal, vol. 116, pp. 191-196, 2014.

[10] M. Ghalkhani and S. Shahrokhian, "Adsorptive stripping differential pulse voltammetric determination of mebendazole at a graphene nanosheets and carbon nanospheres/chitosan modified glassy carbon electrode," Sensors and Actuators B: Chemical, vol. 185, pp. 669-674, 2013.

[11] R. O. Kadara, N. Jenkinson, and C. E. Banks, "Characterization and fabrication of disposable screen printed microelectrodes," Electrochemistry Communications, vol. 11, no. 7, pp. 1377-1380, 2009.

[12] B. C. Janegitz, L. H. Marcolino-Junior, S. P. Campana-Filho, R. C. Faria, and O. Fatibello-Filho, "Anodic stripping voltammetric determination of copper (II) using a functionalized carbon nanotubes paste electrode modified with crosslinked chitosan," Sensors and Actuators B: Chemical, vol. 142, no. 1, pp. 260-266, 2009.

[13] V. I. P. Zanini, R. E. Giménez, O. E. L. Perez, B. A. L. de Mishima, and C. D. Borsarelli, "Enhancement of amperometric response to tryptophan by proton relay effect of chitosan adsorbed on glassy carbon electrode," Sensors and Actuators B: Chemical, vol. 209, pp. 391-398, 2015.
[14] X. Luo, J. Zeng, S. Liu, and L. Zhang, "An effective and recyclable adsorbent for the removal of heavy metal ions from aqueous system: magnetic chitosan/cellulose microspheres," Bioresource technology, vol. 194, pp. 403-406, 2015.
[15] H. H. Ngo, W. Guo, J. Zhang, S. Liang, C. Ton-That, and X. Zhang, "Typical low cost biosorbents for adsorptive removal of specific organic pollutants from water," Bioresource technology, vol. 182, pp. 353-363, 2015.
[16] K.-H. Wu, H.-M. Lo, J.-C. Wang, S.-Y. Yu, and B.-D. Yan, "Electrochemical detection of heavy metal pollutant using crosslinked chitosan/carbon nanotubes thin film electrodes," Materials Express, vol. 7, no. 1, pp. 15-24, 2017.
[17] E. Khaled, H. Hassan, I. Habib, and R. Metelka, "Chitosan modified screen-printed carbon electrode for sensitive analysis of heavy metals," Int. J. Electrochem. Sci, vol. 5, no. 2, pp. 158-167, 2010.
[18] J.-H. Hwang, X. Wang, S. Jung, Y. Son, W. H. Lee, and H. J. Cho, "Enhanced electrochemical detection of multi-heavy metal ions using a biopolymer-coated planar carbon electrode," in Sensors Applications Symposium (SAS), 2018 IEEE, 2018, pp. 1-6: IEEE.
[19] S. Yasmeen, M. K. Kabiraz, B. Saha, M. Qadir, M. A. Gafur, and S. M. Masum, "Chromium (VI) ions removal from tannery effluent using chitosan-microcrystalline cellulose composite as adsorbent," Int. Res. J. Pure Appl. Chem, vol. 10, no. 4, pp. 1-14, 2016.
[20] Y. Wei, R. Yang, J.-H. Liu, and X.-J. Huang, "Selective detection toward Hg (II) and Pb (II) using polypyrrole/carbonaceous nanospheres modified screen-printed electrode," Electrochimica Acta, vol. 105, pp. 218-223, 2013.
[21] N. Koper, L. Leston, T. M. Baker, C. Curry, and P. Rosa, "Effects of ambient noise on detectability and localization of avian songs and tones by observers in grasslands," Ecology and evolution, vol. 6, no. 1, pp. 245-255, 2016.
[22] W. H. Lee, D. G. Wahman, and J. G. Pressman, "Amperometric carbon fiber nitrite microsensor for in situ biofilm monitoring," Sensors and Actuators B: Chemical, vol. 188, pp. 1263-1269, 2013.
[23] C. Martinez-Huitle, N. S. Fernandes, M. Cerro-Lopez, and M. Quiroz, "Determination of trace metals by differential pulse voltammetry at chitosan modified electrodes," Portugaliae Electrochimica Acta, vol. 28, no. 1, pp. 39-49, 2010.
[24] V. J. Vilar, C. M. Botelho, R. J. Martins, and R. A. Boaventura, "Continuous biosorption of single and binary metal solutions in a fixed-bed column using algae gelidium and granulated algal waste from agar extraction," Water Resources Research Progress, pp. 275-296, 2008.
[25] G. Sanna, M. I. Pilo, P. C. Piu, A. Tapparo, and R. Seeber, "Determination of heavy metals in honey by anodic stripping voltammetry at microelectrodes," Analytica Chimica Acta, vol. 415, no. 1-2, pp. 165-173, 2000.

That which is claimed is:

1. A water sensor device for detecting heavy metal in a water sample, the water sensor device comprising:
a substrate;
a reference electrode on the substrate;
a counter electrode on the substrate;
at least one multi-layer electrode on the substrate and being between the reference electrode and the counter electrode, the counter electrode curving around the at least one multi-layer electrode;
the at least one multi-layer electrode comprising
an electrically conductive layer on the substrate,
an electrode layer on the electrically conductive layer, the electrode layer being directly on the electrically conductive layer and contacting the substrate on opposite sides of the electrically conductive layer, and
an insulator layer contacting the electrode layer and the substrate, and defining an opening over the electrode layer;
a biopolymer-metal composite film on the at least one multi-layer electrode and directly on the insulator layer, the biopolymer-metal composite film extending through the opening and contacting the electrode layer and the insulator layer, the biopolymer-metal composite film comprising a metal and a biopolymer, the metal comprising iron, the biopolymer comprising a chitosan material, a width of the opening being less than a width of the biopolymer-metal composite film; and
circuitry coupled to the at least one multi-layer electrode and configured to apply a sensing signal to the at least one multi-layer electrode to detect the metal in the water sample, the heavy metal comprising at least lead.

2. The water sensor device of claim 1 wherein the electrode layer comprises carbon.

3. The water sensor device of claim 1 wherein the electrode layer comprises gold.

4. The water sensor device of claim 1 wherein the circuitry is configured to generate the sensing signal to comprise a square-wave anodic stripping voltammetry (SWASV) sensing signal.

5. The water sensor device of claim 1 wherein the substrate comprises a dielectric material.

6. The water sensor device of claim 5 wherein the dielectric material comprises a polymer plastic material.

7. The water sensor device of claim 1 further comprising:
first, second, and third electrically conductive traces respectively coupled to the counter electrode, the reference electrode, and the at least one multi-layer electrode; and
first, second, and third contact pads respectively coupled to the first, second, and third electrically conductive traces, the first, second, and third contact pads being on a first end of the substrate, the counter electrode, the reference electrode, and the at least one multi-layer electrode being on a second end of the substrate, the second end being opposite to the first end.

8. The water sensor device of claim 1 wherein the counter electrode comprises a distal end being spaced apart from the reference electrode.

9. The water sensor device of claim 1 wherein the counter electrode is C-shaped.

10. The water sensor device of claim 1 wherein the circuitry is configured to apply the sensing signal to the at least one multi-layer electrode to simultaneously detect a plurality of heavy metals.

11. A water sensor device for detecting heavy metal in a water sample, the water sensor device comprising:
a substrate comprising a dielectric material;
a reference electrode on the substrate;
a counter electrode on the substrate;
at least one multi-layer electrode on the substrate and being between the reference electrode and the counter electrode, the counter electrode curving around the at least one multi-layer electrode;

the at least one multi-layer electrode comprising
an electrically conductive layer on the substrate,
an electrode layer on the electrically conductive layer, the electrode layer being directly on the electrically conductive layer and contacting the substrate on opposite sides of the electrically conductive layer, and
an insulator layer contacting the electrode layer and the substrate, and defining an opening over the electrode layer;
a biopolymer-metal composite film on the at least one multi-layer electrode and directly on the insulator layer, the biopolymer-metal composite film extending through the opening and contacting the electrode layer and the insulator layer, the biopolymer-metal composite film comprising a metal and a biopolymer, the metal comprising iron, the biopolymer comprising a chitosan material, a width of the opening being less than a width of the biopolymer-metal composite film; and
circuitry coupled to the at least one multi-layer electrode and configured to apply a sensing signal to the at least one multi-layer electrode to detect the metal in the water sample, the heavy metal comprising at least lead, the electrode layer comprising carbon.

12. The water sensor device of claim 11 wherein the circuitry is configured to generate the sensing signal to comprise a square-wave anodic stripping voltammetry (SWASV) sensing signal.

13. The water sensor device of claim 11 wherein the dielectric material comprises a polymer plastic material.

14. The water sensor device of claim 11 further comprising:
first, second, and third electrically conductive traces respectively coupled to the counter electrode, the reference electrode, and the at least one multi-layer electrode; and
first, second, and third contact pads respectively coupled to the first, second, and third electrically conductive traces, the first, second, and third contact pads being on a first end of the substrate, the counter electrode, the reference electrode, and the at least one multi-layer electrode being on a second end of the substrate, the second end being opposite to the first end.

15. The water sensor device of claim 11 wherein the counter electrode comprises a distal end being spaced apart from the reference electrode.

16. The water sensor device of claim 11 wherein the counter electrode is C-shaped.

17. The water sensor device of claim 11 wherein the circuitry is configured to apply the sensing signal to the at least one multi-layer electrode to simultaneously detect a plurality of heavy metals.

18. A water sensor device for detecting heavy metal in a water sample, the water sensor device comprising:
a substrate comprising a dielectric material;
a reference electrode on the substrate;
a counter electrode on the substrate;
at least one multi-layer electrode on the substrate and being between the reference electrode and the counter electrode, the counter electrode curving around the at least one multi-layer electrode;
the at least one multi-layer electrode comprising
an electrically conductive layer on the substrate,
an electrode layer on the electrically conductive layer, the electrode layer being directly on the electrically conductive layer and contacting the substrate on opposite sides of the electrically conductive layer, and
an insulator layer contacting the electrode layer and the substrate, and defining an opening over the electrode layer;
a biopolymer-metal composite film on the at least one multi-layer electrode and directly on the insulator layer, the biopolymer-metal composite film extending through the opening and contacting the electrode layer and the insulator layer, the biopolymer-metal composite film comprising a metal and a biopolymer, the metal comprising iron, the biopolymer comprising a chitosan material, a width of the opening being less than a width of the biopolymer-metal composite film; and
circuitry coupled to the at least one multi-layer electrode and configured to apply a sensing signal to the at least one multi-layer electrode to detect the metal in the water sample, the heavy metal comprising at least lead, the electrode layer comprising gold.

19. The water sensor device of claim 18 wherein the circuitry is configured to generate the sensing signal to comprise a square-wave anodic stripping voltammetry (SWASV) sensing signal.

20. The water sensor device of claim 18 wherein the dielectric material comprises a polymer plastic material.

* * * * *